United States Patent [19]
Hofmann et al.

[11] Patent Number: 6,159,729
[45] Date of Patent: Dec. 12, 2000

[54] SYNTHETIC HPV6/11 HYBRID L1 DNA ENCODING HUMAN PAPILLOMAVIRUS TYPE 11 L1 PROTEIN

[75] Inventors: Kathryn J. Hofmann, Collegeville; Kathrin U. Jansen, Fort Washington; Michael P. Neeper, Collegeville; Joseph G. Joyce, Lansdale; Hugh A. George, Schwenksville; E. Dale Lehman, Lansdale, all of Pa.

[73] Assignee: Merck & Co., Ltd., Rahway, N.J.

[21] Appl. No.: 08/913,462

[22] PCT Filed: Mar. 26, 1996

[86] PCT No.: PCT/US96/04117

§ 371 Date: Jan. 26, 1998

§ 102(e) Date: Jan. 26, 1998

[87] PCT Pub. No.: WO96/30520

PCT Pub. Date: Oct. 3, 1996

Related U.S. Application Data

[63] Continuation of application No. 08/413,572, Mar. 30, 1995, abandoned, which is a continuation of application No. 08/413,571, Mar. 30, 1995, abandoned.

[51] Int. Cl.⁷ .............................. C12N 15/11; C12N 15/81
[52] U.S. Cl. ...................... 435/320.1; 536/23.72
[58] Field of Search .............................. 424/186.1, 204.1; 435/69.1, 69.3, 235.1, 320.1; 514/2, 44; 530/387.9, 388.3, 389.4; 536/23.1, 23.72

[56] References Cited

PUBLICATIONS

Zaret, K. S. et al.; Mutationally Altered 3' Ends of Yeast CYC1 mRNA Affect Transcript Stability and Translational Efficiency; J. Mol. Biol.; vol. 176; (1984); pp. 107–135.

Russo, P.; *Saccharomyces cerevisiae* mRNA 3' End Forming Signals are also Involved in Transcription Termination; Yeast; vol. 11: (1995); pp. 447–453.

Thalenfeld, B. E. et al.; olil Transcripts in Wild Type and in a Cytoplasmic "Petite" Mutant of Yeast; the Journal of Biological Chemistry; vol. 258; No. 23; Issue of Dec. 10; (1983); pp. 14065–14068.

Lang, W. H. et al.; A Model for Transcription Termination by RNA Polymerase I; Cell; vol. 79; (1994); pp. 527–534.

Heidmann, S. et al.; Flexibility and Interchangeability of Polyadenylation Signals in *Saccharomyces cerevisiae*; Mol. Cell. Biology; vol. 14; No. 7; (1994); pp. 4633–4642.

Brambilla, A. et al.; A simple signal element mediates transcription termination and mRNA 3' end formation in the DEG1 gene of *Saccharomyces cerevisiae*; Mol. Gen. Genet; vol. 254; (1997); pp. 681–688.

Henikoff, S. et al.; Transcription Terminates in Yeast Distal to a Control Sequence; Cell; vol. 33; (1983); pp. 607–614.

Zaret, K. S. et al.; DNA Sequence Required for Efficient Transcription Termination in Yeast; Cell; vol. 28; (1982); pp. 563–573.

Rose et al. (1993) Expression of human papillomavirus type 11 L1 protein in insect cells: in vivo and in vitro assembly of viruslike particles. J. Virol. 67:1936–1944, Apr. 1993.

*Primary Examiner*—Nancy Degen
*Assistant Examiner*—Robert Schwartzman
*Attorney, Agent, or Firm*—Joanne M. Giesser; Jack L. Tribble

[57] ABSTRACT

The present invention is directed to a synthetic DNA molecule encoding purified human papillomavirus type 11 L1 protein and derivatives thereof.

7 Claims, 12 Drawing Sheets

```
                       10         20         30         40         50
Lowy-16L1      1  ATGTCTCTTT GGCTGCCTAG TGAGGCCACT GTCTACTTGC CTCCTGTCCC   50
hpv1611.gb     1  ATGTCTCTTT GGCTGCCTAG TGAGGCCACT GTCTACTTGC CTCCTGTCCC   50
hpv1611.mr1    1  ATGTCTCTTT GGCTGCCTAG TGAGGCCACT GTCTACTTGC CTCCTGTCCC   50

60         70         80         90        100
Lowy-16L1     51  AGTATCTAAG GTTGTAAGCA CGGATGAATA TGTTGCACGC ACAAACATAT  100
hpv1611.gb    51  AGTATCTAAG GTTGTAAGCA CGGATGAATA TGTTGCACGC ACAAACATAT  100
hpv1611.mr1   51  AGTATCTAAG GTTGTAAGCA CGGATGAATA TGTTGCACGC ACAAACATAT  100

110        120        130        140        150
Lowy-16L1    101  ATTATCATGC AGGAACATCC AGACTACTTG CAGTTGGACA TCCCTATTTT  150
hpv1611.gb   101  ATTATCATGC AGGAACATCC AGACTACTTG CAGTTGGACA TCCCTATTTT  150
hpv1611.mr1  101  ATTATCATGC AGGAACATCC AGACTACTTG CAGTTGGACA TCCCTATTTT  150

160        170        180        190        200
Lowy-16L1    151  CCTATTAAAA AACCTAACAA TAACAAAATA TTAGTTCCTA AAGTATCAGG  200
hpv1611.gb   151  CCTATTAAAA AACCTAACAA TAACAAAATA TTAGTTCCTA AAGTATCAGG  200
hpv1611.mr1  151  CCTATTAAAA AACCTAACAA TAACAAAATA TTAGTTCCTA AAGTATCAGG  200

210        220        230        240        250
Lowy-16L1    201  ATTACAATAC AGGGTATTTA GAATACATTT ACCTGACCCC AATAAGTTTG  250
hpv1611.gb   201  ATTACAATAC AGGGTATTTA GAATACATTT ACCTGACCCC AATAAGTTTG  250
hpv1611.mr1  201  ATTACAATAC AGGGTATTTA GAATACATTT ACCTGACCCC AATAAGTTTG  250

260        270        280        290        300
Lowy-16L1    251  GTTTTCCTGA CACCTCATTT TATAATCCAG ATACACAGCG GCTGGTTTGG  300
hpv1611.gb   251  GTTTTCCTGA CACCTCATTT TATAATCCAG ATACACAGCG GCTGGTTTGG  300
hpv1611.mr1  251  GTTTTCCTGA CACCTCATTT TATAATCCAG ATACACAGCG GCTGGTTTGG  300

310        320        330        340        350
Lowy-16L1    301  GCCTGTGTAG GTGTTGAGGT AGGTCGTGGT CAGCCATTAG GTGTGGGCAT  350
hpv1611.gb   301  GCCTGTGTAG GTGTTGAGGT AGGTCGTGGT CAGCCATTAG GTGTGGGCAT  350
hpv1611.mr1  301  GCCTGTGTAG GTGTTGAGGT AGGTCGTGGT CAGCCATTAG GTGTGGGCAT  350

360        370        380        390        400
Lowy-16L1    351  TAGTGGCCAT CCTTTATTAA ATAAATTGGA TGACACAGAA AATGCTAGTG  400
hpv1611.gb   351  TAGTGGCCAT CCTTTATTAA ATAAATTGGA TGACACAGAA AATGCTAGTG  400
hpv1611.mr1  351  TAGTGGCCAT CCTTTATTAA ATAAATTGGA TGACACAGAA AATGCTAGTG  400

410        420        430        440        450
Lowy-16L1    401  CTTATGCAGC AAATGCAGGT GTGGATAATA GAGAATGTAT ATCTATGGAT  450
hpv1611.gb   401  CTTATGCAGC AAATGCAGGT GTGGATAATA GAGAATGTAT ATCTATGGAT  450
hpv1611.mr1  401  CTTATGCAGC AAATGCAGGT GTGGATAATA GAGAATGTAT ATCTATGGAT  450
```

FIG.2A

```
                    460        470        480        490        500
Lowy-16L1     451 TACAAACAAA CACAATTGTG TTTAATTGGT TGCAAACCAC CTATAGGGGA 500
hpv1611.gb    451 TACAAACAAA CACAATTGTG TTTAATTGGT TGCAAACCAC CTATAGGGGA 500
hpv1611.mr1   451 TACAAACAAA CACAATTGTG TTTAATTGGT TGCAAACCAC CTATAGGGGA 500

510        520        530        540        550
Lowy-16L1     501 ACACTGGGGC AAAGGATCCC CATGTACCAA TGTTGCAGTA AATCCAGGTG 550
hpv1611.gb    501 ACACTGGGGC AAAGGATCCC CATGTACCAA TGTTGCAGTA AATCCAGGTG 550
hpv1611.mr1   501 ACACTGGGGC AAAGGATCCC CATGTACCAA TGTTGCAGTA AATCCAGGTG 550

560        570        580        590        600
Lowy-16L1     551 ATTGTCCACC ATTAGAGTTA ATAAACACAG TTATTCAGGA TGGTGATATG 600
hpv1611.gb    551 ATTGTCCACC ATTAGAGTTA ATAAACACAG TTATTCAGGA TGGTGATATG 600
hpv1611.mr1   551 ATTGTCCACC ATTAGAGTTA ATAAACACAG TTATTCAGGA TGGTGATATG 600

610        620        630        640        650
Lowy-16L1     601 GTTGATACTG GCTTTGGTGC TATGGACTTT ACTACATTAC AGGCTAACAA 650
hpv1611.gb    601 GTTGATACTG GCTTTGGTGC TATGGACTTT ACTACATTAC AGGCTAACAA 650
hpv1611.mr1   601 GTTGATACTG GCTTTGGTGC TATGGACTTT ACTACATTAC AGGCTAACAA 650

660        670        680        690        700
Lowy-16L1     651 AAGTGAAGTT CCACTGGATA TTTGTACATC TATTTGCAAA TATCCAGATT 700
hpv1611.gb    651 AAGTGAAGTT CCACTGGATA TTTGTACATC TATTTGCAAA TATCCAGATT 700
hpv1611.mr1   651 AAGTGAAGTT CCACTGGATA TTTGTACATC TATTTGCAAA TATCCAGATT 700

710        720        730        740        750
Lowy-16L1     701 ATATTAAAAT GGTGTCAGAA CCATATGGCG ACAGCTTATT TTTTTATTTA 750
hpv1611.gb    701 ATATTAAAAT GGTGTCAGAA CCATATGGCG ACAGCTTATT TTTTTATTTA 750
hpv1611.mr1   701 ATATTAAAAT GGTGTCAGAA CCATATGGCG ACAGCTTATT TTTTTATTTA 750

760        770        780        790        800
Lowy-16L1     751 CGAAGGGAAC AAATGTTTGT TAGACATTTA TTTAATAGGG CTGGTACTGT 800
hpv1611.gb    751 CGAAGGGAAC AAATGTTTGT TAGACATTTA TTTAATAGGG CTGGTACTGT 800
hpv1611.mr1   751 CGAAGGGAAC AAATGTTTGT TAGACATTTA TTTAATAGGG CTGGTGCTGT 800

810        820        830        840        850
Lowy-16L1     801 TGGTGAAAAT GTACCAGACG ATTTATACAT TAAAGGCTCT GGGTCTACTG 850
hpv1611.gb    801 TGGTGAAAAT GTACCAGACG ATTTATACAT TAAAGGCTCT GGGTCTACTG 850
hpv1611.mr1   801 TGGTGAAAAT GTACCAGACG ATTTATACAT TAAAGGCTCT GGGTCTACTG 850

860        870        880        890        900
Lowy-16L1     851 CAAATTTAGC CAGTTCAAAT TATTTTCCTA CACCTAGTGG TTCTATGGTT 900
hpv1611.gb    851 CAAATTTAGC CAGTTCAAAT TATTTTCCTA CACCTAGTGG TTCTATGGTT 900
hpv1611.mr1   851 CAAATTTAGC CAGTTCAAAT TATTTTCCTA CACCTAGTGG TTCTATGGTT 900
```

FIG.2B

```
                        910        920        930        940        950
Lowy-16L1    901 ACCTCTGATG CCCAAATATT CAATAAACCT TATTGGTTAC AACGAGCACA 950
hpv1611.gb   901 ACCTCTGATG CCCAAATATT CAATAAACCT TATTGGTTAC AACGAGCACA 950
hpv1611.mr1  901 ACCTCTGATG CCCAAATATT CAATAAACCT TATTGGTTAC AACGAGCACA 950

960        970        980        990       1000
Lowy-16L1    951 GGGCCACAAT AATGGCATTT GTTGGGGTAA CCAACTATTT GTTACTGTTG 1000
hpv1611.gb   951 GGGCCACAAT AATGGCATTT GTTGGGGTAA CCAACTATTT GTTACTGTTG 1000
hpv1611.mr1  951 GGGCCACAAT AATGGCATTT GTTGGGGTAA CCAACTATTT GTTACTGTTG 1000

1010       1020       1030       1040       1050
Lowy-16L1   1001 TTGATACTAC ACGCAGTACA AATATGTCAT TATGTGCTGC CATATCTACT 1050
hpv1611.gb  1001 TTGATACTAC ACGCAGTACA AATATGTCAT TATGTGCTGC CATATCTACT 1050
hpv1611.mr1 1001 TTGATACTAC ACGCAGTACA AATATGTCAT TATGTGCTGC CATATCTACT 1050

1060       1070       1080       1090       1100
Lowy-16L1   1051 TCAGAAACTA CATATAAAAA TACTAACTTT AAGGAGTACC TACGACATGG 1100
hpv1611.gb  1051 TCAGAAACTA CATATAAAAA TACTAACTTT AAGGAGTACC TACGACATGG 1100
hpv1611.mr1 1051 TCAGAAACTA CATATAAAAA TACTAACTTT AAGGAGTACC TACGACATGG 1100

1110       1120       1130       1140       1150
Lowy-16L1   1101 GGAGGAATAT GATTTACAGT TTATTTTTCA ACTGTGCAAA ATAACCTTAA 1150
hpv1611.gb  1101 GGAGGAATAT GATTTACAGT TTATTTTTCA ACTGTGCAAA ATAACCTTAA 1150
hpv1611.mr1 1101 GGAGGAATAT GATTTACAGT TTATTTTTCA ACTGTGCAAA ATAACCTTAA 1150

1160       1170       1180       1190       1200
Lowy-16L1   1151 CTGCAGACGT TATGACATAC ATACATTCTA TGAATTCCAC TATTTTGGAG 1200
hpv1611.gb  1151 CTGCAGACGT TATGACATAC ATACATTCTA TGAATTCCAC TATTTTGGAG 1200
hpv1611.mr1 1151 CTGCAGACGT TATGACATAC ATACATTCTA TGAATTCCAC TATTTTGGAG 1200

1210       1220       1230       1240       1250
Lowy-16L1   1201 GACTGGAATT TTGGTCTACA ACCTCCCCCA GGAGGCACAC TAGAAGATAC 1250
hpv1611.gb  1201 GACTGGAATT TTGGTCTACA ACCTCCCCCA GGAGGCACAC TAGAAGATAC 1250
hpv1611.mr1 1201 GACTGGAATT TTGGTCTACA ACCCCCCCCA GGAGGCACAC TAGAAGATAC 1250

1260       1270       1280       1290       1300
Lowy-16L1   1251 TTATAGGTTT GTAAC  CC AGGCAATTGC TTGTCAAAAA CATACACCTC 1300
hpv1611.gb  1251 TTATAGGTTT GTAAC  CC AGGCAATTGC TTGTCAAAAA CATACACCTC 1300
hpv1611.mr1 1251 TTATAGGTTT GTAACATCCC AGGCAATTGC TTGTCAAAAA CATACACCTC 1300

1310       1320       1330       1340       1350
Lowy-16L1   1301 CAGCACCTAA AGAAGATGAT CCCCTTAAAA AATACACTTT TTGGGAAGTA 1350
hpv1611.gb  1301 CAGCACCTAA AGAAGATGAT CCCCTTAAAA AATACACTTT TTGGGAAGTA 1350
hpv1611.mr1 1301 CAGCACCTAA AGAAGAT    CCCCTTAAAA AATACACTTT TTGGGAAGTA 1350
```

FIG.2C

```
                1360       1370       1380       1390       1400
Lowy-16L1    1351 AATTTAAAGG AAAAGTTTTC TGCAGACCTA GATCAGTTTC CTTTAGGACG 1400
hpv1611.gb   1351 AATTTAAAGG AAAAGTTTTC TGCAGACCTA GATCAGTTTC CTTTAGGACG 1400
hpv1611.mrl  1351 AATTTAAAGG AAAAGTTTTC TGCAGACCTA GATCAGTTTC CTTTAGGACG 1400

1410       1420       1430       1440       1450
Lowy-16L1    1401 CAAATTTTTA CTACAAGCAG GATTGAAGGC CAAACCAAAA TTTACATTAG 1450
hpv1611.gb   1401 CAAATTTTTA CTACAAGCAG GATTGAAGGC CAAACCAAAA TTTACATTAG 1450
hpv1611.mrl  1401 CAAATTTTTA CTACAAGCAG GATTGAAGGC CAAACCAAAA TTTACATTAG 1450

1460       1470       1480       1490       1500
Lowy-16L1    1451 GAAAACGAAA AGCTACACCC ACCACCTCAT CTACCTCTAC AACTGCTAAA 1500
hpv1611.gb   1451 GAAAACGAAA AGCTACACCC ACCACCTCAT CTACCTCTAC AACTGCTAAA 1500
hpv1611.mrl  1451 GAAAACGAAA AGCTACACCC ACCACCTCAT CTACCTCTAC AACTGCTAAA 1500

1510       1520       1530       1540       1550
Lowy-16L1    1501 CGCAAAAAAC GTAAGCTGTA .......... .......... .......... 1550
hpv1611.gb   1501 CGCAAAAAAC GTAAGCTGTA A......... .......... .......... 1550
hpv1611.mrl  1501 CGCAAAAAAC GTAAGCTGTA A......... .......... .......... 1550
```

FIG.2D

```
           10         20         30         40         50         60
    ATGTGGCGGC CTAGCGACAG CACAGTATAT GTGCCTCCTC CTAACCCTGT ATCCAAAGTT
           70         80         90        100        110        120
    GTTGCCACGG ATGCTTATGT TAAACGCACC AACATATTTT ATCATGCCAG CAGTTCTAGA
          130        140        150        160        170        180
    CTTCTTGCAG TGGGTCATCC TTATTATTCC ATAAAAAAGG TTAACAAAAC TGTTGTGCCA
          190        200        210        220        230        240
    AAGGTGTCAG GATATCAATA CAGAGTATTT AAGGTGGTGT TACCAGATCC TAACAAATTT
          250        260        270        280        290        300
    GCATTGCCTG ACTCGTCTCT TTTTGATCCC ACAACACAAC GTTTGGTATG GGCATGCACA
          310        320        330        340        350        360
    GGCCTAGAGG TGGGCCGGGG ACAGCCATTA GGTGTGGGTG TAAGTGGACA TCCTTTACTA
          370        380        390        400        410        420
    AATAAATATG ATGATGTTGA AAATTCAGGG GGTTACGGTG GTAACCCTGG ACAGGATAAC
          430        440        450        460        470        480
    AGGGTTAATG TAGGTATGGA TTATAAACAA ACACAATTAT GCATGGTTGG ATGTGCCCCC
          490        500        510        520        530        540
    CCTTTGGGCG AGCATTGGGG TAAAGGTACA CAGTGTAGTA ATACATCTGT ACAGAATGGT
          550        560        570        580        590        600
    GACTGCCCGC CCTTAGAACT TATTACCAGT GTTATACAGG ATGGCGATAT GGTTGACACA
          610        620        630        640        650        660
    GGCTTTGGTG CTATGAATTT TGCTGATTTG CAGACCAATA AATCAGATGT TCCTCTTGAC
          670        680        690        700        710        720
    ATATGTGGCA CTGTATGTAA ATATCCAGAT TATTTACAAA TGGCTGCAGA CCCATATGGT
          730        740        750        760        770        780
    GATAGATTAT TTTTTTATCT ACGGAAGGAA CAAATGTTTG CCAGACATTT TTTTAACAGG
          790        800        810        820        830        840
    GCTGGTACCG TGGGGGAACC TGTGCCTGAT GATCTTTTAG TTAAGGGTGG TAACAATCGC
          850        860        870        880        890        900
    TCGTCTGTAG CGAGTAGTAT ATATGTTCAC ACCCCAAGCG GCTCTTTGGT GTCCTCTGAG
          910        920        930        940        950        960
    GCACAATTGT TTAATAAGCC ATATTGGCTA CAAAAAGCCC AGGGACATAA CAATGGTATT
          970        980        990       1000       1010       1020
    TGTTGGGGTA ATCATCTGTT TGTTACTGTG GTAGATACCA CACGCAGTAC CAACATGACA
         1030       1040       1050       1060       1070       1080
    TTATGTGCAT CCGTATCTAA ATCTGCCACA TACACCAATT CTGATTATAA AGAGTACATG
         1090       1100       1110       1120       1130       1140
    CGTCATGTGG AAGAGTTTGA TTTACAATTT ATTTTTCAAT TATGTAGCAT TACATTGTCT
         1150       1160       1170       1180       1190       1200
    GCTGAAGTAA TGGCCTATAT TCACACAATG AATCCCTCTG TTCTCGAAGA CTGGAACTTT
         1210       1220       1230       1240       1250       1260
    GGGTTATCGC CTCCCCCAAA TGGTACACTC GAGGATACCT ATAGGTATGT GCAGTCACAG
```

FIG. 8A

```
          1270       1280       1290       1300       1310       1320
     GCCATTACCT GTCAAAAGCC CACTCCTGAA AAGGAAAAGC AAGATCCCTA TAAGGACATG
          1330       1340       1350       1360       1370       1380
     AGTTTTTGGG AGGTTAATTT AAAAGAAAAG TTTTCTAGTG AATTGGATCA GTTTCCTTTG
          1390       1400       1410       1420       1430       1440
     GGACGCAAGT TTTTGTTACA AAGTGGATAT AGGGGACGGA CCTCTGCTCG TACCGGTATT
          1450       1460       1470       1480       1490       1500
     AAGCGCCCTG CTGTTTCCAA ACCCTCTACT GCCCCTAAAC GTAAGCGCAC CAAAACTAAA
          1510       1520       1530       1540       1550       1560
     AAGTAA.... .......... .......... .......... .......... ..........
```

FIG. 8B

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 164 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GAAGATCTCA CAAAACAAAA TGTGGCGGCC TAGCGACAGC ACAGTATATG TGCCTCCTCC      60

TAACCCTGTA TCCAAAGTTG TTGCCACGGA TGCTTATGTT AAACGCACCA ACATATTTTA     120

TCATGCCAGC AGTTCTAGAC TTCTTGCAGT GGGTCATCCT TATT                     164
```

(2) INFORMATION FOR SEQ ID NO:2:

(i) SEQUENCE CHARACTERISTICS:
      (A) LENGTH: 156 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

```
ATTCCATAAA AAAGGTTAAC AAAACTGTTG TGCCAAAGGT GTCAGGATAT CAATACAGAG      60

TATTTAAGGT GGTGTTACCA GATCCTAACA AATTTGCATT GCCTGACTCG TCTCTTTTTG     120

ATCCCACAAC ACAACGTTTG GTATGGGCAT GCATGT                              156
```

(2) INFORMATION FOR SEQ ID NO:3:

(i) SEQUENCE CHARACTERISTICS:
      (A) LENGTH: 136 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

```
ACATGCATGC ACAGGCCTAG AGGTGGGCCG GGGACAGCCA TTAGGTGTGG GTGTAAGTGG      60

ACATCCTTTA CTAAATAAAT ATGATGATGT TGAAAATTCA GGGGGTTACG GTGGTAACCC     120

TGGACAGGAT AACAGG                                                    136
```

(2) INFORMATION FOR SEQ ID NO:4:

(i) SEQUENCE CHARACTERISTICS:
      (A) LENGTH: 127 base pairs
      (B) TYPE: nucleic acid (C) STRANDEDNESS: single
                (D) TOPOLOGY: linear (ii) MOLECULE TYPE: cDNA (xi) SEQUENCE DESCRIPTION: SEQ ID NO:4:

GTTAATGTAG GTATGGATTA TAAACAAACA CAATTATGCA TGGTTGGATG TGCCCCCCCT        60

TTGGGCGAGC ATTGGGGTAA AGGTACACAG TGTAGTAATA CATCTGTACA GAATGGTGAC       120

TGCCCGC                                                                127

(2) INFORMATION FOR SEQ ID NO:5:

(i) SEQUENCE CHARACTERISTICS:
                (A) LENGTH: 125 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:5:

CCTTAGAACT TATTACCAGT GTTATACAGG ATGGCGATAT GGTTGACACA GGCTTTGGTG        60

CTATGAATTT TGCTGATTTG CAGACCAATA AATCAGATGT TCCTCTTGAC ATATGTGGCA       120

CTGTA                                                                  125

(2) INFORMATION FOR SEQ ID NO:6:

(i) SEQUENCE CHARACTERISTICS:
                (A) LENGTH: 116 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:6:

TGTAAATATC CAGATTATTT ACAAATGGCT GCAGACCCAT ATGGTGATAG ATTATTTTTT        60

TATCTACGGA AGGAACAAAT GTTTGCCAGA CATTTTTTTA ACAGGGCTGG TACCCC          116

(2) INFORMATION FOR SEQ ID NO:7:

(i) SEQUENCE CHARACTERISTICS:
                (A) LENGTH: 124 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:7:

GGGGTACCGT GGGGAACCT GTGCCTGATG ATCTTTTAGT TAAGGGTGGT AACAATCGCT         60

CGTCTGTAGC GAGTAGTATA TATGTTCACA CCCCAAGCGG CTCTTTGGTG TCCTCTGAGG       120

CACA                                                                   124

(2) INFORMATION FOR SEQ ID NO:8:

(i) SEQUENCE CHARACTERISTICS:
                (A) LENGTH: 113 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:8:

ATTGTTTAAT AAGCCATATT GGCTACAAAA AGCCCAGGGA CATAACAATG GTATTTGTTG      60

GGGTAATCAT CTGTTTGTTA CTGTGGTAGA TACCACACGC AGTACCAACA TGA            113

(2) INFORMATION FOR SEQ ID NO:9:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CATTATGTGC ATCCGTATCT AAATCTGCCA CATACACCAA TTCTGATTAT AAAGAGTACA      60

TGCGTCATGT GGAAGAGTTT GATTTACAAT TTATTTTTCA ATTATGTAGC ATT            113

(2) INFORMATION FOR SEQ ID NO:10:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

ACATTGTCTG CTGAAGTAAT GGCCTATATT CACACAATGA ATCCCTCTGT TCTCGAGGAC      60

TGGAACTTTG GGTTATCGCC TCCCCCAAAT GGTACACTCG AGCGG                     105

(2) INFORMATION FOR SEQ ID NO:11:

(i) SEQUENCE CHARACTERISTICS:
        (A) LENGTH: 155 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CCGCTCGAGG ATACCTATAG GTATGTGCAG TCACAGGCCA TTACCTGTCA AAAGCCCACT      60

CCTGAAAAGG AAAAGCAAGA TCCCTATAAG GACATGAGTT TTTGGGAGGT TAATTTAAAA     120

GAAAAGTTTT CTAGTGAATT GGATCAGTTT CCTTT                                155

(2) INFORMATION FOR SEQ ID NO:12:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GGGACGCAAG TTTTTGTTAC AAAGTGGATA TAGGGGACGG ACCTCTGCTC GTACCGGTAT      60

TAAGCGCCCT GCTGTTTCCA AACCCTCTAC TGCCCCTAAA CGTAAGCGCA CCAAAACTAA     120

AAAGTAAGAT CTTC                                                       134

(2) INFORMATION FOR SEQ ID NO:13:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
GAAGATCTTA CTTTTTAGTT TTGGTGCGCT TACGTTTAGG GGCAGTAGAG GGTTTGGAAA      60

CAGCAGGGCG CTTAATACCG GTACGAGCAG AGGTCCGTCC CCTATATCCA CTTTGTAACA     120

AAAACTTGCG TCCCAAAGGA AACTGATCCA ATTC                                 154
```

(2) INFORMATION FOR SEQ ID NO:14:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
ACTAGAAAAC TTTTCTTTTA AATTAACCTC CCAAAAACTC ATGTCCTTAT AGGGATCTTG      60

CTTTTCCTTT TCAGGAGTGG GCTTTTGACA GGTAATGGCC TGTGACTGCA CATACCTATA     120

GGTATCCTCG AGCGG                                                     135
```

(2) INFORMATION FOR SEQ ID NO:15:

(i) SEQUENCE CHARACTERISTICS:
        (A) LENGTH: 125 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
CCGCTCGAGT GTACCATTTG GGGGAGGCGA TAACCCAAAG TTCCAGTCCT CGAGAACAGA      60

GGGATTCATT GTGTGAATAT AGGCCATTAC TTCAGCAGAC AATGTAATGC TACATAATTG     120

AAAAA                                                                125
```

(2) INFORMATION FOR SEQ ID NO:16:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
TAAATTGTAA ATCAAACTCT TCCACATGAC GCATGTACTC TTTATAATCA GAATTGGTGT      60

ATGTGGCAGA TTTAGATACG GATGCACATA ATGTCATGTT GGTACTGCGT GTG           113
```

(2) INFORMATION FOR SEQ ID NO:17:

(i) SEQUENCE CHARACTERISTICS:
        (A) LENGTH: 113 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:17:

GTATCTACCA CAGTAACAAA CAGATGATTA CCCCAACAAA TACCATTGTT ATGTCCCTGG     60

GCTTTTTGTA GCCAATATGG CTTATTAAAC AATTGTGCCT CAGAGGACAC CAA            113

(2) INFORMATION FOR SEQ ID NO:18:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AGAGCCGCTT GGGGTGTGAA CATATATACT ACTCGCTACA GACGAGCGAT TGTTACCACC     60

CTTAACTAAA AGATCATCAG GCACAGGTTC CCCCACGGTA CCCC                      104

(2) INFORMATION FOR SEQ ID NO:19:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GGGGTACCAG CCCTGTTAAA AAAATGTCTG GCAAACATTT GTTCCTTCCG TAGATAAAAA     60

AATAATCTAT CACCATATGG GTCTGCAGCC ATTTGTAAAT AATCTGGATA TTTACATACA    120

GTGCCACATA TGTCAA                                                    136

(2) INFORMATION FOR SEQ ID NO:20:

(i) SEQUENCE CHARACTERISTICS:
        (A) LENGTH: 125 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GAGGAACATC TGATTTATTG GTCTGCAAAT CAGCAAAATT CATAGCACCA AAGCCTGTGT     60

CAACCATATC GCCATCCTGT ATAACACTGG TAATAAGTTC TAAGGGCGGG CAGTCACCAT    120

TCTGT                                                                125

(2) INFORMATION FOR SEQ ID NO:21:

(i) SEQUENCE CHARACTERISTICS:
        (A) LENGTH: 127 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
ACAGATGTAT TACTACACTG TGTACCTTTA CCCCAATGCT CGCCCAAAGG GGGGGCACAT        60

CCAACCATGC ATAATTGTGT TGTTTATAA TCCATACCTA CATTAACCCT GTTATCCTGT        120

CCAGGGT                                                                127
```

(2) INFORMATION FOR SEQ ID NO:22:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

```
TACCACCGTA ACCCCCTGAA TTTTCAACAT CATCATATTT ATTTAGTAAA GGATGTCCAC        60

TTACACCCAC ACCTAATGGC TGTCCCCGGC CCACCTCTAG GCCTGTGCAT GCATGT           116
```

(2) INFORMATION FOR SEQ ID NO:23:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
ACATGCATGC CCATACCAAA CGTTGTGTTG TGGGATCAAA AAGAGACGAG TCAGGCAATG        60

CAAATTTGTT AGGATCTGGT AACACCACCT TAAATACTCT GTATTGATAT CCTGACACCT       120

TTGGCACAAC AGTTTTGTTA ACCTTTTTTA TGGAATAATA AGGATGACCC                  170
```

(2) INFORMATION FOR SEQ ID NO:24:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

```
ACTGCAAGAA GTCTAGAACT GCTGGCATGA TAAAATATGT TGGTGCGTTT AACATAAGCA        60

TCCGTGGCAA CAACTTTGGA TACAGGGTTA GGAGGAGGCA CATATACTGT GCTGTCGCTA       120

GGCCGCCACA TTTTGTTTTG TGAGATCTTC                                       150
```

(2) INFORMATION FOR SEQ ID NO:25:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
GGAATTCACA TGCATGCACA GGCCTAG                                           27
```

(2) INFORMATION FOR SEQ ID NO:26:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:26:

GGAATTCGGG GTACCAGCCC TGTTAA                                    26

(2) INFORMATION FOR SEQ ID NO:27:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TCGAAGACTG AACTTTGGG TTATCGCCTC CCCCAAATGG TACAC                 45

(2) INFORMATION FOR SEQ ID NO:28:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

TCGAGTGTAC CATTTGGGGG AGGCGATAAC CCAAAGTTCC AGTCT                45

(2) INFORMATION FOR SEQ ID NO:29:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

CTCAGATCTC ACAAAACAAA ATGTGGCGGC CTAGCGACAG CACAG                45

(2) INFORMATION FOR SEQ ID NO:30:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GAGAGATCTT ACTTTTTGGT TTTGGTACGT TTTCG                           35

(2) INFORMATION FOR SEQ ID NO:31:

(i) SEQUENCE CHARACTERISTICS:
        (A) LENGTH: 34 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:31:

GAGAGATCTT ACCTTTTAGT TTTGGCGCGC TTAC                                           34

(2) INFORMATION FOR SEQ ID NO:32:

(i) SEQUENCE CHARACTERISTICS:
                (A) LENGTH: 31 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:32:

CTTAAAGCTT ATGTCACTTT CTCTTGTATC G                                              31

(2) INFORMATION FOR SEQ ID NO:33:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:33:

TGATAAGCTT GCTCAATGGT TCTCTTCCTC                                                30

(2) INFORMATION FOR SEQ ID NO:34:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:34:

TGGTCATCCC AAATCTTGAA A                                                         21

(2) INFORMATION FOR SEQ ID NO:35:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:35:

CACCGTAGTG TTTGGAAGCG A                                                         21

(2) INFORMATION FOR SEQ ID NO:36:

(i) SEQUENCE CHARACTERISTICS:
                (A) LENGTH: 1521 base pairs
                (B) TYPE: nucleic acid
                (C) STRANDEDNESS: single
                (D) TOPOLOGY: linear (ii) MOLECULE TYPE: other nucleic acid -continued (xi) SEQUENCE DESCRIPTION: SEQ ID NO:36:

```
TTCCATGTGG CGGCCTAGCG ACAGCACAGT ATATGTGCCT CCTCCTAACC CTGTATCCAA      60

AGTTGTTGCC ACGGATGCTT ATGTTAAACG CACCAACATA TTTTATCATG CCAGCAGTTC     120

TAGACTTCTT GCAGTGGGTC ATCCTTATTA TTCCATAAAA AAGGTTAACA AAACTGTTGT     180

GCCAAAGGTG TCAGGATATC AATACAGAGT ATTTAAGGTG GTGTTACCAG ATCCTAACAA     240

ATTTGCATTG CCTGACTCGT CTCTTTTTGA TCCCACAACA CAACGTTTGG TATGGGCATG     300

CACAGGCCTA GAGGTGGGCC GGGGACAGCC ATTAGGTGTG GGTGTAAGTG GACATCCTTT     360

ACTAAATAAA TATGATGATG TTGAAAATTC AGGGGGTTAC GGTGGTAACC CTGGACAGGA     420

TAACAGGGTT AATGTAGGTA TGGATTATAA ACAAACACAA TTATGCATGG TTGGATGTGC     480

CCCCCCTTTG GGCGAGCATT GGGGTAAAGG TACACAGTGT AGTAATACAT CTGTACAGAA     540

TGGTGACTGC CCGCCCTTAG AACTTATTAC CAGTGTTATA CAGGATGGCG ATATGGTTGA     600

CACAGGCTTT GGTGCTATGA ATTTTGCTGA TTTGCAGACC AATAAATCAG ATGTTCCTCT     660

TGACATATGT GGCACTGTAT GTAAATATCC AGATTATTTA CAAATGGCTG CAGACCCATA     720

TGGTGATAGA TTATTTTTTT ATCTACGGAA GGAACAAATG TTTGCCAGAC ATTTTTTTAA     780

CAGGGCTGGT ACCGTGGGGG AACCTGTGCC TGATGATCTT TTAGTTAAGG GTGGTAACAA     840

TCGCTCGTCT GTAGCGAGTA GTATATATGT TCACACCCCA AGCGGCTCTT TGGTGTCCTC     900

TGAGGCACAA TTGTTTAATA AGCCATATTG GCTACAAAAA GCCCAGGGAC ATAACAATGG     960

TATTTGTTGG GGTAATCATC TGTTTGTTAC TGTGGTAGAT ACCACACGCA GTACCAACAT    1020

GACATTATGT GCATCCGTAT CTAAATCTGC CACATACACC AATTCTGATT ATAAAGAGTA    1080

CATGCGTCAT GTGGAAGAGT TTGATTTACA ATTTATTTTT CAATTATGTA GCATTACATT    1140

GTCTGCTGAA GTAATGGCCT ATATTCACAC AATGAATCCC TCTGTTCTCG AAGACTGGAA    1200

CTTTGGGTTA TCGCCTCCCC CAAATGGTAC ACTCGAGGAT ACCTATAGGT ATGTGCAGTC    1260

ACAGGCCATT ACCTGTCAAA AGCCCACTCC TGAAAAGGAA AAGCAAGATC CCTATAAGGA    1320

CATGAGTTTT TGGGAGGTTA ATTTAAAAGA AAAGTTTTCT AGTGAATTGG ATCAGTTTCC    1380

TTTGGGACGC AAGTTTTTGT TACAAAGTGG ATATAGGGGA CGGACCTCTG CTCGTACCGG    1440

TATTAAGCGC CCTGCTGTTT CCAAACCCTC TACTGCCCCT AAACGTAAGC GCACCAAAAC    1500

TAAAAAGTAA TTCGATACAC A                                             1521
```

(2) INFORMATION FOR SEQ ID NO:37:

(i) SEQUENCE CHARACTERISTICS:
        (A) LENGTH: 1521 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:37:

```
TTATGTGGCG GCCTAGCGAC AGCACAGTAT ATGTGCCTCC TCCTAACCCT GTATCCAAAG      60

TTGTTGCCAC GGATGCTTAT GTTACTCGCA CCAACATATT TTATCATGCC AGCAGTTCTA     120

GACTTCTTGC AGTGGGTCAT CCTTATTTTT CCATAAAACG GCTAACAAA ACTGTTGTGC      180

CAAAGGTGTC AGGATATCAA TACAGAGTAT TTAAGGTGGT GTTACCAGAT CCTAACAAAT     240

TTGCATTGCC TGACTCGTCT CTTTTTGATC CCACAACACA ACGTTTGGTA TGGGCATGCA     300

CAGGCCTAGA GGTGGGCCGG GGACAGCCAT TAGGTGTGGG TGTAAGTGGA CATCCTTTCC     360
```

```
TAAATAAATA TGATGATGTT GAAAATTCAG GGAGTGGTGG TAACCCTGGA CAGGATAACA      420

GGGTTAATGT AGGTATGGAT TATAAACAAA CACAATTATG CATGGTTGGA TGTGCCCCCC      480

CTTTGGGCGA GCATTGGGGT AAAGGTAAAC AGTGTACTAA TACACCTGTA CAGGCTGGTG      540

ACTGCCCGCC CTTAGAACTT ATTACCAGTG TTATACAGGA TGGCGATATG GTTGACACAG      600

GCTTTGGTGC TATGAATTTT GCTGATTTGC AGACCAATAA ATCAGATGTT CCTATTGACA      660

TATGTGGCAC TACATGTAAA TATCCAGATT ATTTACAAAT GGCTGCAGAC CCATATGGTG      720

ATAGATTATT TTTTTTTCTA CGGAAGGAAC AAATGTTTGC CAGACATTTT TTTAACAGGG      780

CTGGCGAGGT GGGGGAACCT GTGCCTGATA CTCTTATAAT TAAGGGTAGT GGAAATCGCA      840

CGTCTGTAGG GAGTAGTATA TATGTTAACA CCCCAAGCGG CTCTTTGGTG TCCTCTGAGG      900

CACAATTGTT TAATAAGCCA TATTGGCTAC AAAAAGCCCA GGGACATAAC AATGGTATTT      960

GTTGGGGTAA TCAACTGTTT GTTACTGTGG TAGATACCAC ACGCAGTACC AACATGACAT     1020

TATGTGCATC CGTAACTACA TCTTCCACAT ACACCAATTC TGATTATAAA GAGTACATGC     1080

GTCATGTGGA AGAGTATGAT TTACAATTTA TTTTTCAATT ATGTAGCATT ACATTGTCTG     1140

CTGAAGTAAT GGCCTATATT CACACAATGA ATCCCTCTGT TTTGGAAGAC TGGAACTTTG     1200

GGTTATCGCC TCCCCCAAAT GGTACATTAG AAGATACCTA TAGGTATGTG CAGTCACAGG     1260

CCATTACCTG TCAAAAGCCC ACTCCTGAAA AGGAAAAGCC AGATCCCTAT AAGAACCTTA     1320

GTTTTTGGGA GGTTAATTTA AAAGAAAAGT TTTCTAGTGA ATTGGATCAG TATCCTTTGG     1380

GACGCAAGTT TTTGTTACAA AGTGGATATA GGGGACGGTC CTCTATTCGT ACCGGTGTTA     1440

AGCGCCCTGC TGTTTCCAAA GCCTCTGCTG CCCCTAAACG TAAGCGCGCC AAAACTAAAA     1500

GGTAACAGGT TGGATACCAC A                                              1521

(2) INFORMATION FOR SEQ ID NO:38:

(i) SEQUENCE CHARACTERISTICS:
        (A) LENGTH: 1519 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:38:

TTCCATGTGG CGGCCTAGCG ACAGCACAGT ATATGTGCCT CCTCCCAACC CTGTATCCAA       60

GGTTGTTGCC ACGGATGCGT ATGTTAAACG CACCAACATA TTTTATCATG CCAGCAGTTC      120

TAGACTCCTT GCTGTGGGAC ATCCATATTA CTCTATCAAA AAAGTTAACA AAACAGTTGT      180

ACCAAAGGTG TCTGGATATC AATATAGAGT GTTTAAGGTA GTGTTGCCAG ATCCTAACAA      240

GTTTGCATTA CCTGATTCAT CCCTGTTTGA CCCCACTACA CAGCGTTTAG TATGGGCGTG      300

CACAGGGTTG GAGGTAGGCA GGGGTCAACC TTTAGGCGTT GGTGTTAGTG GGCATCCATT      360

GCTAAACAAA TATGATGATG TAGAAAATAG TGGTGGGTAT GGTGGTAATC CTGGTCAGGA      420

TAATAGGGTT AATGTAGGTA TGGATTATAA ACAAACCCAG CTATGTATGG TGGGCTGTGC      480

TCCACCGTTA GGTGAACATT GGGGTAAGGG TACACAATGT TCAAATACCT CTGTACAAAA      540

TGGTGACTGC CCCCCGTTGG AACTTATTAC CAGTGTTATA CAGGATGGGG ACATGGTTGA      600

TACAGGCTTT GGTGCTATGA ATTTTGCAGA CTTACAAACC AATAAATCGG ATGTTCCCCT      660

TGATATTTGT GGAACTGTCT GCAAATATCC TGATTATTTG CAAATGGCTG CAGACCCTTA      720

TGGTGATAGG TTGTTTTTTT ATTTGCGAAA GGAACAAATG TTTGCTAGAC ACTTTTTTAA      780
```

-continued

| | | | | | |
|---|---|---|---|---|---|
|TAGGGCCGGT|ACTGTGGGGG|AACCTGTGCC|TGATGACCTG|TTGGTAAAAG|GGGGTAATAA 840|
|CAGATCATCT|GTAGCTAGTA|GTATTTATGT|ACATACACCT|AGTGGCTCAT|TGGTGTCTTC 900|
|AGAGGCTCAA|TTATTTAATA|AACCATATTG|GCTTCAAAAG|GCTCAGGGAC|ATAACAATGG 960|
|TATTTGCTGG|GGAAACCACT|TGTTTGTTAC|TGTGGTAGAT|ACCACACGCA|GTACAAATAT 1020|
|GACACTATGT|GCATCTGTGT|CTAAATCTGC|TACATACACT|AATTCAGATT|ATAAGGAATA 1080|
|CATGCGCCAT|GTGGAGGAGT|TTGATTTACA|GTTTATTTTT|CAATTGTGTA|GCATTACATT 1140|
|ATCTGCAGAA|GTCATGGCCT|ATATACACAC|AATGAATCCT|TCTGTTTTGG|AGGACTGGAA 1200|
|CTTTGGTTTA|TCGCCTCCAC|CAAATGGTAC|ACTGGAGGAT|ACTTATAGAT|ATGTACAGTC 1260|
|ACAGGCCATT|ACCTGTCAGA|AACCCACACC|TGAAAAAGAA|AAACAGGATC|CCTATAAGGA 1320|
|TATGAGTTTT|TGGGAGGTTA|ACTTAAAAGA|AAAGTTTTCA|AGTGAATTAG|ATCAGTTTCC 1380|
|CCTTGGACGT|AAGTTTTTAT|TGCAAAGTGG|ATATCGAGGA|CGGACGTCTG|CTCGTACAGG 1440|
|TATAAAGCGC|CCAGCTGTGT|CTAAGCCCTC|TACAGCCCCC|AAACGAAAAC|GTACCAAAAC 1500|
|CAAAAAGTAA|ACGATCACA| | | |1519|

SYNTHETIC HPV6/11 HYBRID L1 DNA ENCODING HUMAN PAPILLOMAVIRUS TYPE 11 L1 PROTEIN

CROSS-RELATED TO OTHER APPLICATIONS

This application is a 371 of PCT/US96/04117, filed Mar. 26, 1997 and a continuation of U.S. Ser. No. 08/413,572 filed Mar. 30, 1995, abandoned, and a continuation of U.S. Ser. No. 08/413,571 filed Mar. 30, 1995, abandoned.

FIELD OF THE INVENTION

The present invention is directed to a synthetic DNA molecule encoding purified human papillomavirus type 11 L1 protein and derivatives thereof.

BRIEF DESCRIPTION OF THE DRAWINGS

FIGS. 2A–2D show the nucleotide sequence of the HPV6/11 hybrid (SEQ ID NO:38), published HPV6a (SEQ ID NO:36) and published HPV11 L1 (SEQ ID NO:37) genes.

FIGS. 8A–8B shows the nucleotide sequence of the HPV6/11 hybrid gene (SEQ ID NO:34).

BACKGROUND OF THE INVENTION

Figure 1:
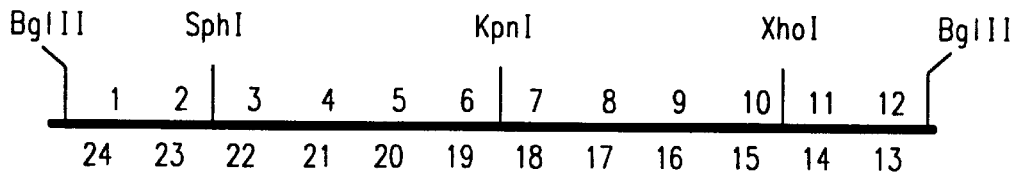
FIG. 1 is a schematic of the construction of the HPV6/11 hybrid L1 gene, using synthetic oligonucleotides.

Papillomavirus (PV) infections occur in a variety of animals, including humans, sheep, dogs, cats, rabbits, monkeys, snakes and cows. Papillomaviruses infect epithelial cells, generally inducing benign epithelial or fibroepithelial tumors at the site of infection. PV are species specific infective agents; a human papillomavirus cannot infect a nonhuman animal.

Papillomaviruses may be classified into distinct groups based on the host that they infect. Human papillomaviruses (HPV) are further classified into more than 70 types based on DNA sequence homology. PV types appear to be type-specific immunogens in that a neutralizing immunity to infection by one type of papillomavirus does not confer immunity against another type of papillomavirus.

In humans, different HPV types cause distinct diseases. HPV types 1, 2, 3, 4, 7, 10 and 26–29 cause benign warts in both normal and immunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause nonmalignant condylomata of the genital or respiratory mucosa. HPV types 16, 18, 31, 33, 35, 45, and 58 cause epithelial dysplasia of the genital mucosa and are associated with the majority of in situ and invasive carcinomas of the cervix, vagina, vulva and anal canal.

Papillomaviruses are small (50–60 nm), nonenveloped, icosahedral DNA viruses that encode for up to eight early and two late genes. The open reading frames (ORFs) of the virus genomes are designated E1 to E8 and L1 and L2, where "E" denotes early and "L" denotes late. L1 and L2 code for virus capsid proteins. The early (E) genes are associated with functions such as viral replication, transcriptional regulation and cellular transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis. Immunological data suggest that most of the L2 protein is internal to the L1 protein within the viral capsomere. The L1 ORF is highly conserved among different papillomaviruses. The L2 proteins are less conserved among different papillomaviruses.

The L1 and L2 genes have been identified as good targets for immunoprophylaxis. Some of the early genes have also been demonstrated to be potential targets of vaccine development. Studies in the cottontail rabbit papillomavirus (CRPV) and bovine papillomavirus (BPV) systems have shown that immunizations with recombinant L1 and/or L2 proteins (produced in bacteria or by using vaccinia vectors) protected animals from viral infection. Expression of papillomavirus L1 genes in baculovirus expression systems or using vaccinia vectors resulted in the assembly of virus-like particles (VLP) which have been used to induce high-titer virus-neutralizing antibody responses that correlate with protection from viral challenge. Furthermore, the L1 and L2 genes have been used to generate vaccines for the prevention and treatment of papillomavirus infections in animals.

The development and commercialization of prophylactic and therapeutic vaccines for PV infection and disease containing L1 protein, L1+L2 proteins, or modified L1 or L1+L2 proteins has been hindered by the lack of large quantities of purified virus and purified protein. Because PV is not readily cultivated in vitro, it is difficult to produce the required amounts of L1 and L2 protein by in vitro propagation of PV. The resultant supply problems make it difficult to characterize PV and PV proteins. Accordingly, it would be useful to develop a readily renewable source of crude PV proteins, especially PV L1 and L2 proteins or modified L1 and L2 proteins. It would also be useful to develop methods of purifying large quantities of the crude papillomavirus proteins to levels of purity suitable for immunological studies and vaccine development. It would also be useful to produce large quantities of papillomavirus proteins having the immunity-conferring properties of the native proteins, such as the conformation of the native protein. In addition, it would be useful to develop methods of analyzing the PV proteins and methods of determining the relative purity of the proteins as well as compositions containing the proteins. Such highly purified proteins would also be useful in the preparation of a variety of reagents useful in the study of PV infection; such reagents include but are not limited to polyclonal antibodies, monoclonal antibodies, and analytical standards.

HPV6 and 11 are causative agents for ~90% of benign genital warts and are only rarely associated with malignancies (Gissmann et al., 1983, PNAS 80, 560–563). HPV6a is considered to be the most abundant HPV6 subtype in condyloma accuminata (Brown, D. B., et al., J. Clin. Microbiol. 31:1667–1673). Office visits for genital warts (condyloma accuminatum or planum) have been on the rise in recent years. It is estimated that ~10% of the general population (ages 15–49) have genital-tract HPV infections (Koutsky et al. 1988, Epidemiol. Rev. 10, 122–163). While the majority of condylomata is associated with HPV6, in the case of laryngeal papillomatosis, HPV11 is the dominant type. HPV11 replication in the epithelial cells of the respiratory tract stimulates the proliferation of these cells which can lead to isolated lesions of minor clinical relevance or to multiple spreading lesions and recurring disease. Recurrent respiratory papillomatosis, a disease which more often afflicts the juvenile population, can be a life-threatening disease by causing obstructions in the respiratory tract. Recently, an animal model which allows the replication of infectious HPV11, has been developed (Kreider et al. 1985, *Nature* 317, 639–640; Kreider et al. 1987, *J. Virol.* 61, 590–593). The model enabled the identification of conformational neutralizing epitopes on native virions and baculoviru-sexpressed VLPs using monoclonal antibodies (Christensen et al 1990, *J. Virol.* 64, 5678–5681; Christensen and Kreider 1991, *Virus Res.* 21, 169–179; Christensen and Kreider 1993, *Virus Res.* 28, 195–202; Christensen et al. 1994, 75, 2271–2276).

Virus-like particles containing HPV11 L1 protein have been expressed in both insect and mammalian cell systems. Expression of VLPs in yeast cells offers the advantages of being cost-effective and easily adapted to large-scale growth in fermenters. However, the HPV11 L1 protein is expressed at low levels in yeast cells. This was observed to be a result of truncation of the HPV11 L1 mRNA. In contrast, the HPV6 L1 gene is transcribed as full-length mRNA and is expressed to high levels. By modifying the HPV6 L1 DNA to encode the HPV11 L1 protein, it is possible to facilitate the transcription of full-length mRNA resulting in increased HPV11 L1 protein expression. The present invention provides an HPV6/11 hybrid L1 gene sequence as well as a method for the construction of the HPV6/11 hybrid L1 gene using synthetic oligonucleotides. The hybrid gene was designed using the HPV6a L1 sequence (Hofiann, K. J., et al., 1995, *Virology*, accepted for publication) but contains the minimal number of base changes necessary to encode the HPV11 L1 protein. Unlike the wild-type HPV11 L1 gene, the HPV6/11 hybrid gene does not contain yeast-recognized internal transcription termination signals; as a result full-length HPV6/11 mRNA is produced and expression of HPV11 L1 protein is increased.

The present invention is directed to highly purified PV L1 protein. The invention also comprises methods by which recombinant papillomavirus proteins having the immunity-conferring properties of the native papillomavirus proteins are produced and purified. The present invention is directed to the production of prophylactic and therapeutic vaccines for papillomavirus infection. Electron microscopy and binding to conformational antibodies demonstrate that the recombinant proteins of the present invention are capable of forming virus-like particles.

SUMMARY OF THE INVENTION

The present invention is directed to a synthetic DNA molecule encoding purified human papillomavirus type 11 L1 protein and derivatives thereof.

DETAILED DESCRIPTION OF THE INVENTION

The present invention is directed to a synthetic DNA molecule encoding purified human papillomavirus type 11 L1 protein and derivatives thereof. Various embodiments of the invention include but are not limited to recombinant HPV DNA molecules, RNA complementary to the recombinant HPV DNA molecules, proteins encoded by the recombinant DNA molecules, antibodies to the recombinant DNA molecules and related proteins, compositions comprising the DNA, RNA, proteins orantibodies, methods of using the DNA, RNA, proteins or antibodies as well as derivatives thereof. Such derivatives include but are not limited to peptides and proteins encoded by the DNA, antibodies to the DNA or antibodies to the proteins encoded by the DNA, vaccines comprising the DNA or vaccines comprising proteins encoded by the DNA, immunological compositions comprising the DNA or the proteins encoded by the DNA, kits containing the DNA or RNA derived from the DNA or proteins encoded by the DNA.

HPV6 and 11 are causative agents for ~90% of benign genital warts and are only rarely associated with malignancies (Gissmann et al., 1983, *PNAS* 80, 560–563). Office visits for genital warts (condyloma accuminatum or planum) have been on the rise in the last years and it is estimated that ~10% of the general population (ages 15–49) have genital-tract HPV infections (Koutsky et al. 1988, *Epidemiol.* Rev. 10, 122–163). While the majority of condylomata is associated with HPV6, in the case of laryngeal papillomatosis, HPV11 is the dominant type. HPV11 replication in the epithelial cells of the respiratory tract stimulates the proliferation of these cells which can lead to isolated lesions of minor clinical relevance or to multiple spreading lesions and recurring disease. Recurrent respiratory papillomatosis, a disease which more often afflicts the juvenile population, can be a life-threatening disease by causing obstructions in the respiratory tract. Recently, an animal model which allows the replication of infectious HPV11, has been developed (Kreider et al. 1985, *Nature* 317, 639–640; Kreider et al. 1987, *J. Virol.* 61, 590–593). The model enabled the identification of conformational neutralizing epitopes on native virions and baculovirus-expressed VLPs using monoclonal antibodies (Christensen et al. 1990, *J. Virol* 64, 5678–5681; Christensen and Kreider 1991, *Virus-Res.* 21, 169–179; Christensen and Kreider 1993, *Virus Res.* 28, 195–202; Christensen et al. 1994, 75, 2271–2276).

The development and commercialization of prophylactic and therapeutic vaccines for PV infection and disease containing L1 protein, L1+L2 proteins, or modified L1 or L1+L2 proteins has been hindered by the lack of large quantities of purified virus and purified protein. Because PV is not readily cultivated in vitro, it is difficult to produce the required amounts of L1 and L2 protein by in vitro propagation of PV. The difficulties associated with in vitro cultivation of PV also result in difficulties in chemical, immunological and biological characterization of PV and PV proteins. Accordingly, it would be useful to develop a readily renewable source of crude PV proteins, especially PV L1 and L2 proteins or modified L1 and L2 proteins. It would also be useful to develop methods of purifying large quantities of the crude papillomavirus proteins to levels of purity suitable for immunological studies and vaccine development. It would also be useful to produce large quantities of papillomavirus proteins having the immunity-conferring properties of the native proteins, such as the conformation of the native protein. In addition, it would be useful to develop methods of analyzing the PV proteins and methods of determining the relative purity of the proteins as well as compositions containing the proteins. Such highly purified proteins would also be useful in the preparation of a variety of reagents useful in the study of PV infection; such reagents include but are not limited to polyclonal antibodies, monoclonal antibodies, and analytical standards.

Virus-like particles containing HPV11 L1 protein have been expressed in both insect and mammalian cell systems.

Expression of VLPs in yeast cells offers the advantages of being cost-effective and easily adapted to large-scale growth in fermenters. However, the HPV11 L1 protein is expressed at low levels in yeast cells. This was observed to be a result of truncation of the HPV11 L1 mRNA. In contrast, the HPV6 L1 gene is transcribed as full-length mRNA and is expressed to high levels. By modifying the HPV6 L1 DNA to encode the HPV11 L1 protein, it is possible to facilitate the transcription of full-length mRNA resulting in increased HPV11 L1 protein expression. The present invention provides an HPV6/11 hybrid L1 gene as well as a method for the construction of the HPV6/11 hybrid L1 gene using synthetic oligonucleotides. The hybrid gene was designed using the HPV6a L1 sequence but contains the minimal number of base changes necessary to encode the HPV11 L1 protein. Unlike the wild-type HPV11 L1 gene, the HPV6/11 hybrid gene does not contain yeast-recognized internal transcription termination signals, resulting in higher levels of mRNA and consequently increased HPV11 L1 protein expression.

Pharmaceutically useful compositions comprising the DNA or proteins encoded by the DNA may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein or VLP. Such compositions may contain proteins or VLP derived from more than one type of HPV.

Therapeutic or diagnostic compositions of the invention are administered to an individual in amounts sufficient to treat or diagnose PV infections. The effective amount may vary according to a variety of factors such as the individual's condition, weight, sex and age. Other factors include the mode of administration. Generally, the compositions will be administered in dosages ranging from about 1 mcg to about 1 mg.

The pharmaceutical compositions may be provided to the individual by a variety of routes such as subcutaneous, topical, oral, mucosal, intravenous and intramuscular.

The vaccines of the invention comprise DNA, RNA or proteins encoded by the DNA that contain the antigenic determinants necessary to induce the formation of neutralizing antibodies in the host. Such vaccines are also safe enough to be administered without danger of clinical infection; do not have toxic side effects; can be administered by an effective route; are stable; and are compatible with vaccine carriers.

The vaccines may be administered by a variety of routes, such as orally, parenterally, subcutaneously, mucosally, intravenously or intramuscularly. The dosage administered may vary with the condition, sex, weight, and age of the individual; the route of administration; and the type PV of the vaccine. The vaccine may be used in dosage forms such as capsules, suspensions, elixirs, or liquid solutions. The vaccine may be formulated with an immunologically acceptable carrier.

The vaccines are administered in therapeutically effective amounts, that is, in amounts sufficient to generate a immunologically protective response. The therapeutically effective amount may vary according to the type of PV. The vaccine may be administered in single or multiple doses.

The purified proteins of the present invention may be used in the formulation of immunogenic compositions. Such compositions, when introduced into a suitable host, are capable of inducing an immune response in the host.

The purified proteins of the invention or derivatives thereof may be used to generate antibodies. The term "antibody" as used herein includes both polyclonal and monoclonal antibodies, as well as fragments thereof, such as, Fv, Fab and F(ab)2 fragments that are capable of binding antigen or hapten.

The proteins and protein derivatives of the present invention may be used to serotype HPV infection and HPV screening. The purified proteins, VLP and antibodies lend themselves to the formulation of kits suitable for the detection and serotyping of HPV. Such a kit would comprise a compartmentalized carrier suitable to hold in close confinement at least one container. The carrier may further comprise reagents such as L1 or L2 proteins or VLPs derived from recombinant HPV6/11 or other recombinant HPV type DNA molecules or antibodies directed against these proteins. The carrier may also contain means for detection such as labeled antigen or enzyme substrates or the like.

The purified proteins are also useful as immunological standards, molecular weight markers and molecular size markers.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis.

As used herein, a "functional derivative" of the HPV6/11 hybrid gene is a compound that possesses a biological activity (either functional or structural) that is substantially similar to the biological activity of HPV6/11. The term "functional derivatives" is intended to include the "fragments," "variants," "degenerate variants," "analogs" and "homologues" or to "chemical derivatives" of HPV6/11.

The term "analog" refers to a molecule substantially similar in function to either the entire HPV6/11 molecule or to a fragment thereof.

The cloned HPV6/11 DNA or fragments thereof obtained through the methods described herein may be recombinantly expressed by molecular cloning into an expression vector containing a suitable promoter and other appropriate transcription regulatory elements, and transferred into prokaryotic or eukaryotic host cells to produce recombinant HPV11. Techniques for such manipulations are fully described in Sambrook, J., et al., supra, and are known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells. Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express HPV6/11 DNA or fragments thereof in mammalian cells. Commercially available mammalian expression vectors which may be suitable for recombinant HPV6/11 DNA expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express HPV6/11 DNA or fragments thereof in bacterial cells. Commercially available bacterial expression vectors which may be suitable for recombinant HPV6/11 DNA expression include, but are not limited to pET11a (Novagen), lambda gt11 (Invitrogen), pcDNAII (Invitrogen), pKK223-3 (Pharmacia).

A variety of fungal cell expression vectors may be used to express HPV6/11 or fragments thereof in fungal cells. Commercially available fungal cell expression vectors which may be suitable for recombinant HPV6/11 DNA expression include but are not limited to pYES2 (Invitrogen), Pichia expression vector (Invitrogen) and Hansenula expression (Rhein Biotech, Dusseldorf, Germany).

A variety of insect cell expression vectors may be used to express HPV6/11 DNA or fragments thereof in insect cells. Commercially available insect cell expression vectors which may be suitable for recombinant expression of HPV6/11 DNA include but are not limited to pBlue Bac III (Invitrogen).

An expression vector containing HPV6/11 DNA or fragments thereof may be used for expression of HPV11 proteins or fragments of HPV11 proteins in a cell, tissue, organ, or animal. Animal, as used herein, includes humans. Host cells may be prokaryotic or eukaryotic, including but not limited to bacteria such as E. Coli, fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK⁻) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, lipofection, protoplast fusion, and electroporation. The expression vector-containing cells are clonally propagated and individually analyzed to determine whether they produce HPV11 protein. Identification of HPV11 expressing host cell clones may be done by several means, including but not limited to immunological reactivity with anti-HPV11 antibodies.

Expression of HPV DNA fragments may also be performed using in vitro produced synthetic mRNA or native mRNA. Synthetic mRNA or mRNA isolated from cells expressing HPV6/11 hybrid DNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of HPV11 protein in a host cell, HPV11 protein may be recovered to provide HPV11 protein in purified form. Several HPV11 purification procedures are available and suitable for use. As described herein, recombinant HPV11 protein may be purified from cell lysates and extracts by various combinations of, or individual application of salt fractionation, ion exchange chromatography, size exclusion chromatography, hydroxylapatite adsorption chromatography and hydrophobic interaction chromatography.

In addition, recombinant HPV11 protein may be separated from other cellular proteins by use of an immunoaffinity column made with monoclonal or polyclonal antibodies specific for full length nascent HPV11, or polypeptide fragments of HPV11. Monoclonal and polyclonal antibodies may be prepared according to a variety of methods known in the art. Monoclonal or monospecific antibody as used herein is defined as a single antibody species or multiple antibody species with homogenous binding characteristics for HPV11. Homogenous binding as used herein refers to the ability of the antibody species to bind to a specific antigen or epitope.

It is apparent to those skilled in the art that the methods for producing monospecific antibodies may be utilized to produce antibodies specific for HPV polypeptide fragments, or full-length nascent HPV polypeptides. Specifically, it is apparent to those skilled in the art that monospecific antibodies may be generated which are specific for the fully functional HPV proteins or fragments thereof.

The present invention is also directed to methods for screening for compounds which modulate the expression of DNA or RNA encoding HPV as well as the function(s) of HPV11 protein in vivo. Compounds which modulate these activities may be DNA, RNA, peptides, proteins, or non-proteinaceous organic molecules. Compounds may modulate by increasing or attenuating the expression of DNA or RNA encoding HPV11, or the function of HPV11 protein. Compounds that modulate the expression of DNA or RNA encoding HPV11 or the function of HPV11 protein may be detected by a variety of assays. The assay may be a simple "yes/no" assay to determine whether there is a change in expression or function. The assay may be made quantitative by comparing the expression or function of a test sample with the levels of expression or function in a standard sample.

Kits containing HPV6/11 hybrid DNA, fragments of HPV6/11 hybrid DNA, antibodies to HPV6/11 DNA or HPV11 protein, HPV6/11 hybrid RNA or HPV11 protein may be prepared. Such kits are used to detect DNA which hybridizes to HPV6/11 DNA or to detect the presence of HPV11 protein or peptide fragments in a sample. Such characterization is useful for a variety of purposes including but not limited to forensic analyses and epidemiological studies.

Nucleotide sequences that are complementary to the HPV6/11 DNA sequence may be synthesized for antisense therapy. These antisense molecules may be DNA, stable derivatives of DNA such as phosphorothioates or methylphosphonates, RNA, stable derivatives of RNA such as 2'-O-alkylRNA, or other HPV6/11 antisense oligonucleotide mimetics. HPV6/11 antisense molecules may be introduced into cells by microinjection, liposome encapsulation or by expression from vectors harboring the antisense sequence. HPV6/11 antisense therapy may be particularly useful for the treatment of diseases where it is beneficial to reduce HPV11 activity.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the HPV11 or its activity while minimizing any potential toxicity. In addition, co-administration or sequential administration of other agents may be desirable.

Advantageously, compounds of the present invention may be administered in a single dose, or the total dosage may be administered in several divided doses. Furthermore, compounds for the present invention may be administered via a variety of routes including but not limited to intranasally, transdermally, by suppository, orally, and the like.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and may be administered in admixture with suitable pharmaceutical diluents, excipients or carriers (collectively referred to herein as "carrier" materials) suitably selected with respect to the intended form of administration, that is, oral tablets, capsules, elixirs, syrup, suppositories, gels and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include without limitation, starch, gelatin, natural sugars such as glucose or beta-lactose, corn sweeteners, natural and synthetic gums such as acacia, tragacanth, sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The following examples illustrate the present invention without, however, limiting the same thereto.

EXAMPLE 1

Construction of the Synthetic L1 Gene

The 1.5 kbp open reading frame of HPV11 L1 was constructed using synthetic DNA oligomers ordered from Midland Reagent Company. These oligomers were supplied containing 5' terminal phosphates. A total of 24 oligomers were required and are listed below:

```
#241-1                                     (SEQ ID NO:1)
5'GAAGATCTCACAAAACAAAATGTGGCGGCCTAGC
GACAGCACAGTATATGTGCCTCCTCCTAACCCTGT
ATCCAAAGTTGTTGCCACGGATGCTTATGTTAAAC
GCACCAACATATTTTATCATGCCAGCAGTTCTAGA
```

-continued
CTTCTTGCAGTGGGTCATCCTTATT3'

2412 (SEQ ID NO:2)
5'ATTCCATAAAAAAGGTTAACAAAACTGTTGTGCC
AAAGGTGTCAGGATATCAATACAGAGTATTTAAGG
TGGTGTTACCAGATCCTAACAAATTTGCATTGCCT
GACTCGTCTCTTTTTGATCCCACAACACAACGTTT
GGTATGGGCATGCATGT3'

241-3 (SEQ ID NO:3)
5'ACATGCATGCACAGGCCTAGAGGTGGGCCGGGGA
CAGCCATTAGGTGTGGGTGTAAGTGGACATCCTTT
ACTAAATAAATATGATGATGTTGAAAATTCAGGGG
GTTACGGTGGTAACCCTGGACAGGATAACAGG3'

241-4 (SEQ ID NO:4)
5'GTTAATGTAGGTATGGATTATAAACAAACACAAT
TATGCATGGTTGGATGTGCCCCCCCTTTGGGCGAG
CATTGGGGTAAAGGTACACAGTGTAGTAATACATC
TGTACAGAATGGTGACTGCCCGC3'

241-5 (SEQ ID NO:5)
5'CCTTAGAACTTATTACCAGTGTTATACAGGATGG
CGATATGGTTGACACAGGCTTTGGTGCTATGAATT
TTGCTGATTTGCAGACCAATAAATCAGATGTTCCT
CTTGACATATGTGGCACTGTA3'

241-6 (SEQ ID NO:6)
5'TGTAAATATCCAGATTATTTACAAATGGCTGCAG
ACCCATATGGTGATAGATTATTTTTTTATCTACGG
AAGGAACAAATGTTTGCCAGACATTTTTTTAACAG
GGCTGGTACCCC3'

241-7 (SEQ ID NO:7)
5'GGGGTACCGTGGGGAACCTGTGCCTGATGATCT
TTTAGTTAAGGGTGGTAACAATCGCTCGTCTGTAG
CGAGTAGTATATATGTTCACACCCCAAGCGGCTCT
TTGGTGTCCTCTGAGGCACA3'

241-8 (SEQ ID NO:8)
5'ATTGTTTAATAAGCCATATTGGCTACAAAAAGCC
CAGGGACATAACAATGGTATTTGTTGGGGTAATCA
TCTGTTTGTTACTGTGGTAGATACCACACGCAGTA
CCAACATGA3'

241-9 (SEQ ID NO:9)
5'CATTATGTGCATCCGTATCTAAATCTGCCACATA
CACCAATTCTGATTATAAAGAGTACATGCGTCATG
TGGAAGAGTTTGATTTACAATTTATTTTTCAATTA
TGTAGCATT3'

241-10 (SEQ ID NO:10)
5'ACATTGTCTGCTGAAGTAATGGCCTATATTCACA
CAATGAATCCCTCTGTTCTCGAGGACTGGAACTTT
GGGTTATCGCCTCCCCCAAATGGTACACTCGAGCG
G3'

241-11 (SEQ ID NO:11)
5'CCGCTCGAGGATACCTATAGGTATGTGCAGTCAC
AGGCCATTACCTGTCAAAAGCCCACTCCTGAAAAG
GAAAAGCAAGATCCCTATAAGGACATGAGTTTTTG
GGAGGTTAATTTAAAAGAAAAGTTTTCTAGTGAAT
TGGATCAGTTTCCTTT3'

241-12 (SEQ ID NO:12)
5'GGGACGCAAGTTTTTGTTACAAAGTGGATATAGG
GGACGGACCTCTGCTCGTACCGGTATTAAGCGCCC
TGCTGTTTCCAAACCCTCTACTGCCCCTAAACGTA
AGCGCACCAAAACTAAAAAGTAAGATCTTC3'

241-13 (SEQ ID NO:13)
5'GAAGATCTTACTTTTTAGTTTTGGTGCGCTTACG
TTTAGGGGCAGTAGAGGGTTTGGAAACAGCAGGGC
GCTTAATACCGGTACGAGCAGAGGTCCGTCCCCTA
TATCCACTTTGTAACAAAAACTTGCGTCCCAAAGG
AAACTGATCCAATTC3'

241-14 (SEQ ID NO:14)
5'ACTAGAAAACTTTTCTTTTAAATTAACCTCCCAA
AAACTCATGTCCTTATAGGGATCTTGCTTTTCCTT

-continued
TTCAGGAGTGGGCTTTTGACAGGTAATGGCCTGTG
ACTGCACATACCTATAGGTATCCTCGAGCGG3'

241-15 (SEQ ID NO:15)
5'CCGCTCGAGTGTACCATTTGGGGGAGGCGATAAC
CCAAAGTTCCAGTCCTCGAGAACAGAGGGATTCAT
TGTGTGAATATAGGCCATTACTTCAGCAGACAATG
TAATGCTACATAATTGAAAAA3'

241-16 (SEQ ID NO:16)
5'TAAATTGTAAATCAAACTCTTCCACATGACGCAT
GTACTCTTTATAATCAGAATTGGTGTATGTGGCAG
ATTTAGATACGGATGCACATAATGTCATGTTGGTA
CTGCGTGTG3'

241-17 (SEQ ID NO:17)
5'GTATCTACCACAGTAACAAACAGATGATTACCCC
AACAAATACCATTGTTATGTCCCTGGGCTTTTTGT
AGCCAATATGGCTTATTAAACAATTGTGCCTCAGA
GGACACCAA3'

241-18 (SEQ ID NO:18)
5'AGAGCCGCTTGGGGTGTGAACATATATACTACTC
GCTACAGACGAGCGATTGTTACCACCCTTAACTAA
AAGATCATCAGGCACAGGTTCCCCCACGGTACCCC
3'

241-19 (SEQ ID NO:19)
5'GGGGTACCAGCCCTGTTAAAAAAATGTCTGGCAA
ACATTTGTTCCTTCCGTAGATAAAAAAATAATCTA
TCACCATATGGGTCTGCAGCCATTTGTAAATAATC
TGGATATTTACATACAGTGCCACATATGTCAA3'

241-20 (SEQ ID NO:20)
5'GAGGAACATCTGATTTATTGGTCTGCAAATCAGC
AAAATTCATAGCACCAAAGCCTGTGTCAACCATAT
CGCCATCCTGTATAACACTGGTAATAAGTTCTAAG
GGCGGGCAGTCACCATTCTGT3'

241-21 (SEQ ID NO:21)
5'ACAGATGTATTACTACACTGTGTACCTTTACCCC
AATGCTCGCCCAAAGGGGGGGCACATCCAACCATG
CATAATTGTGTTTGTTTATAATCCATACCTACATT
AACCCTGTTATCCTGTCCAGGGT3'

241-22 (SEQ ID NO:22)
5'TACCACCGTAACCCCCTGAATTTTCAACATCATC
ATATTTATTTAGTAAAGGATGTCCACTTACACCCA
CACCTAATGGCTGTCCCCGGCCCACCTCTAGGCCT
GTGCATGCATGT3'

241-23 (SEQ ID NO:23)
5'ACATGCATGCCCATACCAAACGTTGTGTTGTGGG
ATCAAAAAGAGACGAGTCAGGCAATGCAAATTTGT
TAGGATCTGGTAACACCACCTTAAATACTCTGTAT
TGATATCCTGACACCTTTGGCACAACAGTTTTGTT
AACCTTTTTTATGGAATAATAAGGATGACCC3'

241-24 (SEQ ID NO:24)
5'ACTGCAAGAAGTCTAGAACTGCTGGCATGATAAA
ATATGTTGGTGCGTTTAACATAAGCATCCGTGGCA
ACAACTTTGGATACAGGGTTAGGAGGAGGCACATA
TACTGTGCTGTCGCTAGGCCGCCACATTTTGTTTT
GTGAGATCTTC3'

Oligomers forming complementary pairs (#241-1 and #241-24, #241-2 and #241-23, #241-3 and #241-22, #241-4 and #241-21, #241-5 and #241-20, #241-6 and #241-19, #241-7 and #241-18, #241-8 and #241-17, #241-9 and #241-16, #241-10 and #241-15, #241-11 and #241-14, #241-12 and #241-13-FIG. 1) were annealed in separate tubes containing 2.5 mM Tris, pH 7.5, 0.25 mM EDTA. Tubes were heated to 98° C. for 4 min and then placed in 200 ml of 98° C. water in a 250 ml beaker to cool slowly. When the water cooled to room temperature, the annealed pairs were added to tubes as designated: fragment A (oligomer pairs #241-1 & 24, and -2 & 23); fragment B (#241-3 & 22, -4 & 21, -5 & 20, and -6 & 19); fragment C (#241-7 & 18, -8 & 17, -9 & 16 and -10 & 15) and fragment D (#241-11 & 14 and -12 & 13). These oligomer pair mixes were heated to 62° C. for 2 min and then cooled slowly as before. The contents of each tube were ligated overnight at 23° C. using T4 DNA ligase (Boehringer Mannheim, Inc.) and the reagents supplied by the manufacturer.

After ligation, fragment B required PCR amplification to increase the amount of full-length product. This required ten cycles of 94° C., 1 min; 48° C., 1 min; 72° C., 1 min followed by 10 min at 72° C. in an Applied Biosystems theimocycler using Boehringer Mannheim Taq polymerase and the oligomer primers:

5'GGAATTCACATGCATGCACAGGCCTAG 3'  (SEQ ID NO:25)

and

5'GGAATTCGGGGTACCAGCCCTGTTAA 3'  (SEQ ID NO:26).

The ligated products and the fragment B PCR product were digested with restriction enzymes (Boehringer Mannheim, Inc.) as follows: fragment A was digested with Bgl II and Sph I; fragment B, Sph I and Kpn I; fragment C, Kpn I and Xho I; and fragment D, Xho I and Bgl II. The digested fragments were separated on low melting point agarose (FMC BioProducts) gels and correctly sized fragments isolated by excision of the band and digestion of the agarose using Agarase™ (Boehringer Mannheim, Inc.) as recommended by the supplier. The fragments A, B and D were recovered by ethanol precipitation and then separately ligated into the vector pSP72 (Promega, Inc.) that had been similarly digested with restriction enzymes to match each fragment being ligated.

The Kpn I Xho I digested fragment C was first ligated to the annealed oligomers

5'TCGAAGACTGGAACTTTGGGTTATCGCCTCCCC(SEQ ID NO:27)
CAAATGGTACAC3';

and

5'TCGAGTGTACCATTTGGGGGAGGCGATAACCCA(SEQ ID NO:28)
AAGTTCCAGTCT3'.

Fragment C was then recleaved with Xho I and the 450 bp Kpn I Xho I fragment was ligated with the Kpn I, Xho I-digested pSP72 vector. The ligation mixes were used to transform Escherichia coli strain DH5 competent cells (Gibco BRL, Gaithersburg, Md.). Transformants were screened for insert-containing clones by colony hybridization (J. Sambrook et al., Molecular Cloning: A Laboratory Manual, 2nd edition, Cold Spring Harbor Laboratory Press, 1989). Plasmid DNA was isolated from the positive clones using a Wizard miniprep kit (Promega Corp.) and then sequenced using an Applied Biosystems 373A DNA Sequencer. Clones containing the correct DNA sequence for each of the four fragments were digested as before to release the fragments from the pSP72 vector. The Kpn I, Xho I-digested fragment C was ligated with the Xho I, Bgl II-digested fragment D and Kpn I, Bgl II-cut pSP72 in a three-way ligation. The ligation products were then used to transform E. coli. Resulting transformants were sequenced and a clone of correct sequence obtained (designated CD). The 750 bp Bgl II Kpn I insert of CD was recleaved from the pSP72 vector and ligated with Bgl II, Sph I digested fragment A and Sph I, Kpn I-digested fragment B in a threeway ligation as before except Bgl II was added to decrease undesired ligation products. The ligation products were separated on agarose gels, the 1.5 kbp fragment was isolated, and was designated D361-1.

EXAMPLE 2

Comparison of Sequences

A comparison of the nucleotide sequence for the HPV6/11 hybrid, HPV6a and HPV11 L1 DNA sequences is shown in FIG. 2. There are a total of 55 nucleotide substitutions made to the HPV6 backbone sequence to convert it to a HPV11-encoding translation frame. In addition, three base pair insertions were added at #411–413 bp to encode the additional amino acid (tyrosine132) found in HPV11 but not HPV6. Together, these changes allow the type 11-specific, conformation-dependent, neutralizing monoclonal antibody (Chemicon 8740 MAb) to bind the L1 protein of the HPV6/11 L1 DNA expressed in yeast. This suggests that the protein from the HPV6/11 hybrid gene appears to be indistinguishable immunologically from native HPV11.

Comparison of the HPV6/11 hybrid DNA sequence to the published HPV11 L1 sequence shows 194 base pair substitutions. There are a considerable number of substitutions relative to the wild type 11 L1 sequence, any combination of which or all changes in total may be what is responsible for the increased type 11 L1 protein expression in yeast.

EXAMPLE 3

DNA Sequencing of the L1 gene

The HPV6/11 L1 gene was sequenced using an Applied Biosystems DNA Sequencer #373A with dye terminator sequencing reactions (PRIZM™ Sequencing Kit) as specified by the manufacturer (ABI, Inc., Foster City, Calif.).

EXAMPLE 4

Construction of HPV6/11 L1, HPV11 L1 and HPV6 L1 Yeast Expression Vectors

Figure 3:
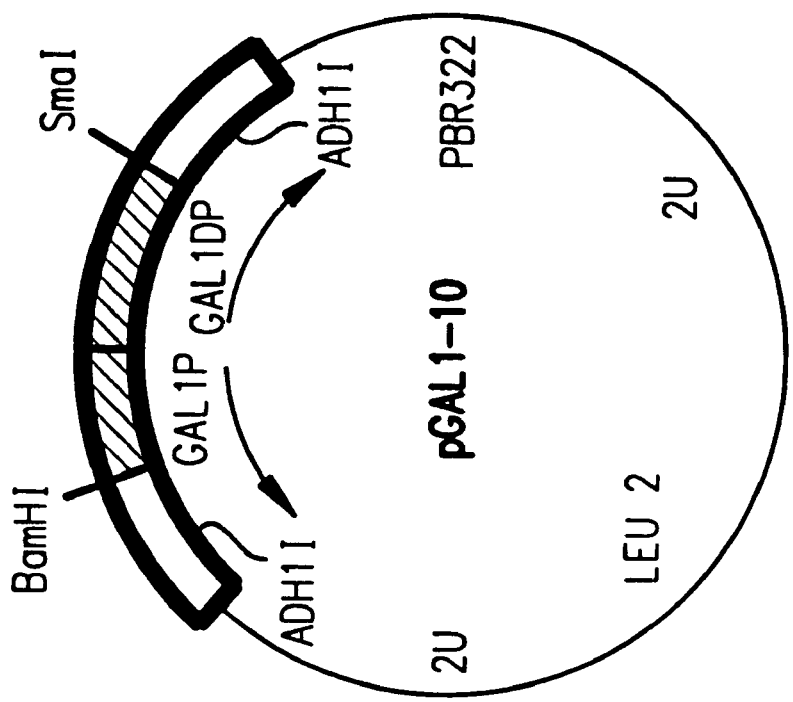
FIG. 3 shows the bidirectional yeast expression vector pGAL1-10 used to express papillomavirus L1 capsid proteins.

The pGAL1-10 yeast expression vector was constructed by isolating a 1.4 kbp Sph I fragment from a pUC18/ bidirectional GAL promoter plasmid which contains the Saccharomyces cerevisiae divergent GAL1–GAL10 promoters from the plasmid pBM272 (provided by Mark Johnston, Washington University, St. Louis, Mo.). The divergent promoters are flanked on each side by a copy of the yeast ADH1 transcriptional terminator (Bennetzen, J. L. and Hall, B. D., 1982, J. Biol. Chem. 257: 3018–3025), a BamHI cloning site located between the GAL1 promoter and the first copy of the ADH1 transcriptional terminator and a SmaI cloning site located between the GAL10 promoter and the second copy of the ADH1 transcriptional terminator. A yeast shuttle vector consisting of pBR322, the yeast LEU2d gene (Erhart, E. and Hollenberg, C. P., 1983, J. Bacteriol. 156: 625–635) and the yeast 2μ plasmid (gift of Benjamin Hall, University of Washington, Seattle, Wash.) (Broach, J. R. and Volkert, F. C., 1991, Circular DNA Plasmids of Yeasts, Cold Spring Harbor Laboratory Press, Cold Spring Harbor, N.Y.) was digested with Sph I and ligated with the 1.4 kbp Sph I divergent GAL promoter fragment resulting in pGAL1-10 (FIG. 3).

The HPV6/11 hybrid L1 DNA encoding the HPV11 L1 protein (sample D361-1 from Example 1) contains a yeast non-translated leader sequence (Kniskem, P. J. et al., 1986, Gene 46: 135–141) immediately upstream to the HPV6/11 L1 initiating methionine codon. The pGAL1-10 plasmid was linearized with BamHI which cuts between the GAL1 promoter and the ADH1 transcription terminator and ligated with the 1.5 kbp, HPV6/11 L1 gene fragment (sample D361-1). E. coli DH5 (Gibco BRL, Inc.) transformants were screened and a pGAL1-10 plasmid containing the HPV6/11 L1 gene was isolated and designated as D362-1.

The wild-type HPV11 (wt-HPV11) DNA was cloned from a condyloma acuminatum lesion (kind gift of Dr. Darron Brown). Total human genomic DNA was extracted and digested with restriction endonucleases. The fraction containing wt-HPV11 DNA was ligated into an *E. coli* cloning vector to be used as a template for PCR. The wt-HPV11 L1 gene was amplified by PCR using Vent polymerase (New England Biolabs, Inc.), 10 cycles of amplification (94° C. 1 min, 48° C. 1 min, 72° C. 1 min 45 sec), and the following oligonucleotide primers which contain flanking Bgl II sites (underlined):

```
sense primer: 5'-CTC AGATCT CAC AAA    (SEQ ID NO:29)
              ACA AAA TGT GGC GGC
              CTA GCG ACA GCA CAG-3' antisense     5'-GAG AGATCT TAC TTT    (SEQ ID NO:30)
primer:       TTG GTT TTG GTA CGT
              TTT CG-3'
```

The sense primer introduces a yeast non-translated leader sequence (Kniskem, P. J. et al., 1986, *Gene* 46: 135–141) immediately upstream to the wt-HPV11 L1 initiating methionine codon (highlighted in bold print). The 1.5 kbp wt-HPV11 L1 PCR product was digested with Bgl II, gel purified and ligated with the BamHI digested pGAL1-10 plasmid to yield plasmid, p329-1.

Total genomic DNA was extracted from an HPV6a-positive, condyloma acuminatum lesion (kind gift of Dr. Darron Brown). The HPV6a L1 gene was amplified by PCR using the biopsy sample DNA as a template, Vent polymerase (New England Biolabs, Inc.), 35 cycles of amplification (94° C. 1 min, 48° C. 1 min, 72° C. 1 min 45 sec), the sense primer listed above for PCR of wt-HPV11 L1 and an antisense primer with the sequence,

```
                                       (SEQ ID NO:31)
5'-GAG AGATCT TAC CTT TTA GTT TTG GCG CGC TTA C-3'.
```

The 1.5 kbp HPV6a L1 PCR product was digested with Bgl II, gel purified and ligated with the BamHI digested pGAL1-10 plasmid to yield plasmid D128.

EXAMPLE 5
Preparation of Strain 1558

Step a: Preparation of Yeast Strain U9

Saccharomyces cerevisiae strain 2150-2-3 (MATalpha, leu2-04, adel, cir°) was obtained from Dr. Leland Hartwell (University of Washington, Seattle, Wash.). Cells of strain 2150-2-3 were propagated overnight at 30° C. in 5 mL of YEHD medium (Carty et al., *J. Ind Micro* 2 (1987) 117–121). The cells were washed 3 times in sterile, distilled water, resuspended in 2 mL of sterile distilled water, and 0.1 mL of cell suspension was plated onto each of six 5-fluoro-orotic acid (FOA) plates in order to select for ura3 mutants (Cold Spring Harbor Laboratory Manual for Yeast Genetics). The plates were incubated at 30° C. The medium contained per 250 mL distilled water: 3.5 g, Difco Yeast Nitrogen Base without amino acids and ammonium sulfate; 0.5 g 5-Fluoro-orotic acid; 25 mg Uracil; and 10.0 g Dextrose.

The medium was sterilized by filtration through 0.2 μm membranes and then mixed with 250 mL of 4% Bacto-Agar (Difco) maintained at 50° C., 10 mL of a 1.2 mg/mL solution of adenine, and 5 mL of L-leucine solution (180 mg/50 mL). The resulting medium was dispensed at 20 mL per petri dish.

After 5 days of incubation, numerous colonies had appeared. Single colonies were isolated by restreaking colonies from the initial FOA plates onto fresh FOA plates which were then incubated at 30° C. A number of colonies from the second set of FOA plates were tested for the presence of the ura3 mutation by replica-plating onto both YEHD plates and uracil-minus plates. The desired result was good growth on YEHD and no growth on uracil-minus medium. One isolate (U9) was obtained which showed these properties. It was stored as a frozen glycerol stock (strain #325) at −70° C. for later use.

Step b: Preparation of a Vector for disruption of the Yeast MNN9 gene

In order to prepare a vector for disruption of the MNN9 gene, it was necessary to first clone the MNN9 gene from *S. cerevisiae* genomic DNA. This was accomplished by standard Polymerase Chain Reaction (PCR) technology. A 5' sense primer and 3' antisense primer for PCR of the full-length MNN9 coding sequence were designed based on the published sequence for the yeast MNN9 gene (Zymogenetics: EPO Patent Application No. 88117834.7, Publication No. 0-314-096-A2). The following oligodeoxynucleotide primers containing flanking HindIII sites (underlined) were used:

```
sense primer: 5'-CTT AAAGCTTAT GTC    (SEQ ID NO:32)
              ACT TTC TCT TGT ATC
              G-3' antisense     5'-TGA TAAGCT TGC TCA   (SEQ ID NO:33)
primer:       ATG GTT CTC TTC CTC-3'
```

The initiating methionine codon for the MNN9 gene is highlighted in bold print. The PCR was conducted using genomic DNA from *S. cerevisiae* strain JRY 188 as template, Taq DNA polymerase (Perkin Elmer) and 25 cycles of amplification (94° C. 1 min., 37° C. 2 min., 72° C. 3 min.). The resulting 1.2 kbp PCR fragment was digested with HindIII, gel-purified, and ligated with HindIII-digested, alkaline-phosphatase treated pUC13 (Pharmacia). The resulting plasmid was designated p1183.

In order to disrupt the MNN9 gene with the yeast URA3 gene, the plasmid pBR322-URA3 (which contains the 1.1 Kbp HindIII fragment encoding the *S. cerevisiae* URA3 gene subcloned into the HindIII site of pBR322) was digested with HindIII and the 1.1 kbp DNA fragment bearing the functional URA3 gene was gel-purified, made bluntended with T4 DNA polymerase, and then ligated with PmlI-digested plasmid p1183 (PmlI cuts within the MNN9 coding sequence). The resulting plasmid p1199 contains a disruption of the MNN9 gene by the functional URA3 gene.

Step c: Construction of U9-derivative strain 1372 containing disruption of MNN9 gene For disruption of the MNN9 gene in strain U9 (#325), 30 μg of plasmid p1199 were digested with HindIII to create a linear mnn9::URA3 disruption cassette. Cells of strain 325 were transformed with the HindIII-digested p1199 DNA by the spheroplast method (Hinnen et al., 1978, *Proc. Natl. Acad. Sci. USA* 75:1929–1933) and transformants were selected on a synthetic agar medium lacking uracil and containing 1.0M sorbitol. The synthetic medium contained, per liter of distilled water: Agar, 20 g; Yeast nitrogen base w/o amino acids, 6.7 g; Adenine, 0.04 g; L-tyrosine, 0.05 g; Sorbitol, 182 g; Glucose, 20 g; and Leucine Minus Solution #2, 10 ml. Leucine Minus Solution #2 contains per liter of distilled water: L-arginine, 2 g; L-histidine, 1 g; L-Leucine, 6 g; L-Isoleucine, 6 g; L-lysine, 4 g; L-methionine, 1 g; L-phenylalanine, 6 g; L-threonine, 6 g; L-tryptophan, 4 g.

The plates were incubated at 30° C. for five days at which time numerous colonies had appeared. Chromosomal DNA preparations were made from 10 colonies and then digested with EcoRI plus HindIII. The DNA digests were then evaluated by Southern blots (J. Sambrook et al., *Molecular Cloning: A Laboratory Manual*, 2nd edition, Cold Spring Harbor Laboratory Press, 1989) using the 1.2 kbp HindIII fragment bearing the MNN9 gene (isolated from plasmid p1199) as a probe. An isolate was identified (strain #1372) which showed the expected DNA band shifts on the Southern blot as well as the extreme dumpiness typically shown by mnn9 mutants.

Step d: Construction of a Vector for Disruption of Yeast HIS3 Gene

In order to construct a disruption cassette in which the *S. cerevisiae* HIS3 gene is disrupted by the URA3 gene, the plasmid YEp6 (K. Struhl et al., 1979, *Proc. Natl. Acad. Sci., USA* 76:1035) was digested with BamHI and the 1.7 kbp BamHI fragment bearing the HIS3 gene was gel-purified, made blunt-ended with T4 DNA polymerase, and ligated with pUC18 which had been previously digested with BamHI and treated with T4 DNA polymerase. The resulting plasmid (designated p1501 or pUC18-HIS3) was digested with NheI (which cuts in the HIS3 coding sequence), and the vector fragment was gel-purified, made blunt-ended with T4 DNA polymerase, and then treated with calf intestine alkaline phosphatase. The URA3 gene was isolated from the plasmid pBR322-URA3 by digestion with HindIII and the 1.1 kbp fragment bearing the URA3 gene was gel-purified, made blunt-ended with T4 DNA polymerase, and ligated with the above pUC18-HIS3 NheI fragment. The resulting plasmid (designated pUC18-his3::URA3 or p1505) contains a disruption cassette in which the yeast HIS3 gene is disrupted by the functional URA3 gene.

Step e: Construction of Vector for Disruption of Yeast PRB1 Gene by the HIS3 Gene Plasmid FP8ΔH bearing the *S. cerevisiae* PRB1 gene was provided by Dr. E. Jones of Carnegie-Mellon Univ. (C. M. Moehle et al., 1987, *Genetics* 115:255–263). It was digested with HindIII plus Xho I and the 3.2 kbp DNA fragment bearing the PRB1 gene was gel-purified and made blunt-ended by treatment with T4 DNA polymerase. The plasmid pUC18 was digested with BamHI, gel-purified and made blunt-ended by treatment with T4 DNA polymerase. The resulting vector fragment was ligated with the above PRB1 gene fragment to yield the plasmid pUC18-PRB1. Plasmid YEp6, which contains the HIS3 gene, was digested with BamHI. The resulting 1.7 kbp BamHI fragment bearing the functional HIS3 gene was gel-purified and then made blunt-ended by treatment with T4 DNA polymerase. Plasmid pUC18-PRB1 was digested with EcoRV plus NcoI which cut within the PRB1 coding sequence and removes the protease B active site and flanking sequence. The 5.7 kbp EcoRV-NcoI fragment bearing the residual 5' and 3'-portions of the PRB1 coding sequence in pUC18 was gel-purified, made blunt-ended by treatment with T4 DNA polymerase, dephosphorylated with calf intestine alkaline phosphatase, and ligated with the blunt-ended HIS3 fragment described above. The resulting plasmid (designated pUC18-prb1::HIS3, stock #1245) contains the functional HIS3 gene in place of the portion of the PRB1 gene which had been deleted above.

Step f: Construction of a U9-related Yeast Strain containing disruptions of both the MNN9 and PRB1 Genes The U9-related strain 1372 which contains a MNN9 gene disruption was described in Example 5c. Clonal isolates of strain 1372 were passaged on FOA plates (as described in Example 5a) to select ura3 mutants. A number of ura3 isolates of strain 1372 were obtained and one particular isolate (strain 12930-190-S1-1) was selected for subsequent disruption of the HIS3 gene. The pUC18-his3::URA3 gene disruption vector (p1505) was digested with XbaI plus EcoRI to generate a linear his3::URA3 disruption cassette and used for transformation of strain 12930-190-S1-1 by the lithium acetate method (*Methods in Enzymology*, 194:290 (1991). Ura$^+$ transformants were selected on synthetic agar medium lacking uracil, restreaked for clonal isolates on the same medium, and then replica-plated onto medium lacking either uracil or histidine to screen for those isolates that were both Ura$^+$ and His$^-$. One isolate (strain 12930-230-1) was selected for subsequent disruption of the PRB1 gene. The PRB1 gene disruption vector (pUC18-prb1::HIS3, stock #1245) was digested with SacI plus XbaI to generate a linear prb1::HIS3 disruption cassette and used for transformation of strain 12930-230-1 by the lithium acetate method. His$^+$ transformants were selected on agar medium lacking histidine and restreaked on the same medium for clonal isolates. Genomic DNA was prepared from a number of the resulting His$^+$ isolates, digested with EcoRI, and then electrophoresed on 0.8% agarose gels. Southern blot analyses were then performed using a radio-labeled 617 bp probe for the PRB1 gene which had been prepared by PCR using the following oligodeoxynucleotide primers:

```
5' TGG TCA TCC CAA ATC TTG AAA 3'    (SEQ ID NO:34);
and
5' CAC CGT AGT GTT TGG AAG CGA 3'    (SEQ ID NO:35)
```

Eleven isolates were obtained which showed the expected hybridization of the probe with a 2.44 kbp prb1::HIS3 DNA fragment. This was in contrast to hybridization of the probe with the 1.59 kbp fragment for the wild-type PRB1 gene. One of these isolates containing the desired prb1::HIS3 disruption was selected for further use and was designated strain #1558.

EXAMPLE 6

Expression of HPV11 L1 and HPV6 L1 in Yeast

Plasmids D362-1 (pGAL1-10+HPV6/11 L1), p329-1 (pGAL1-10+wt-HPV11 L1), D128 (pGAL1-10+HPV6 L1) and pGAL1-10 were used to transform *S. Cerevisiae* strain #1558 (MATa, leu2-04, prb1::HIS3, mnn9::URA3, adel, cir°) by the spheroplast method (Hinnen et al., 1978, *Proc. Natl. Acad. Sci. USA* 75, 1929–1933). The #1558 yeast strain transformed with plasmid D362-1 was designated as strain #1782. For RNA studies, yeast clonal isolates were grown at 30° C. in YEH complex medium (Carty et al., 1987, *J. Ind. Micro.* 2, 117–121) containing 0.1M sorbitol and either 2% glucose or galactose for 26 hours. After harvesting the cells, yeast RNA was extracted using the hot acidic phenol method as described (*Current Protocols in Molecular Biology*, vol. 2, Current Protocols, 1993). For protein analysis, the identical isolates were grown at 30° C. in YEH complex medium containing 0.1M sorbitol, 2% glucose and 2% galactose for 70 hours. After harvesting the cells, the cell pellets were broken with glass beads and cell lysates analyzed for the expression of HPV11 L1 or HPV6 L1 protein by immunoblot analysis.

EXAMPLE 7

Northern Blot Analysis of Yeast Expressed HPV L1 RNAs

Samples containing 10 μg of total RNA were denatured by treatment with glyoxal and DMSO (*Current Protocols in Molecular Biology*, vol. 1, Current Protocols, 1993) and electrophoresed through a phosphate-buffered, 1.2% agarose gel. The RNA was transferred onto a nylon membrane and detected with a $^{32}$P-labeled oligonucleotide that is complementary to both the HPV11 and HPV6 L1 DNA sequences.

Figure 4:
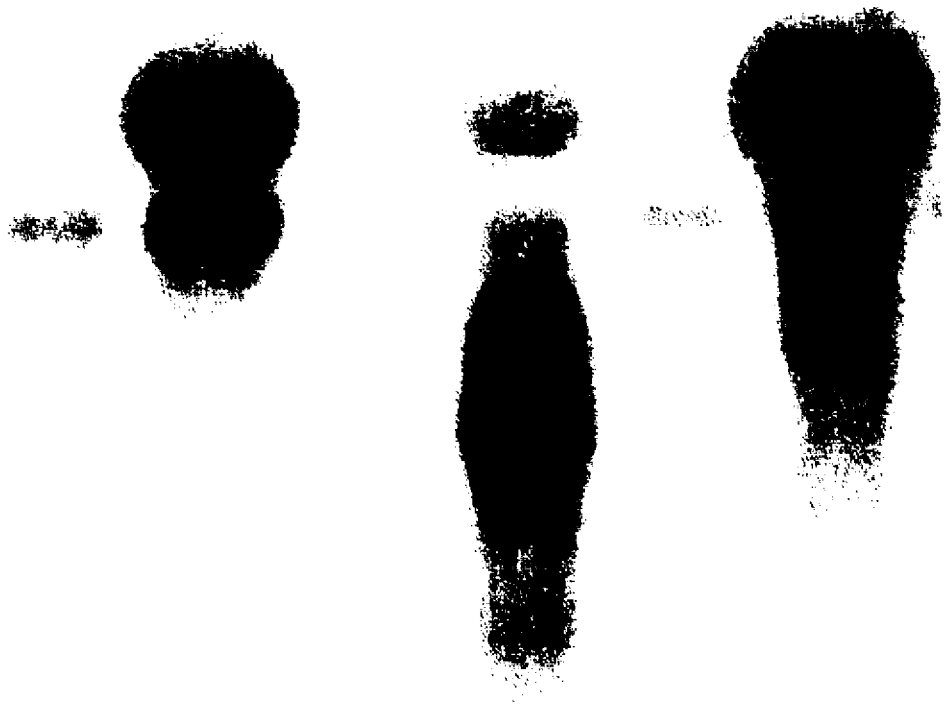
FIG. 4 is a Northern analysis of HPV11 L1 mRNA from yeast.

The Northern blot is shown in FIG. 4. No bands that correspond to the expected size for full-length HPV L1 RNA were detected in the samples grown on glucose medium (lanes 1, 3 and 5). This is expected since glucose represses transcription from the yeast GAL1 promoter. In contrast, samples grown in galactose medium which induces transcription from the GAL1 promoter, show strong HPV L1 RNA signals. The HPV6 L1 was transcribed as a full-length RNA species (lane 2) while the majority of the wild-type (wt)-HPV11 L1 was transcribed as a truncated form (lane 4). This result suggested that a yeast transcription termination signal is located within the wt-HPV11 L1 ORF but is not present in the HPV6 L1 sequence. The RNA transcribed from the HPV6/11 hybrid gene appears to be full-length (lane 6). No HPV specific RNA is detected in the pGAL1-10 control yeast sample (lane 7).

EXAMPLE 8
Western Analysis of Yeast Expressed HPV L1 Proteins

Figure 5:
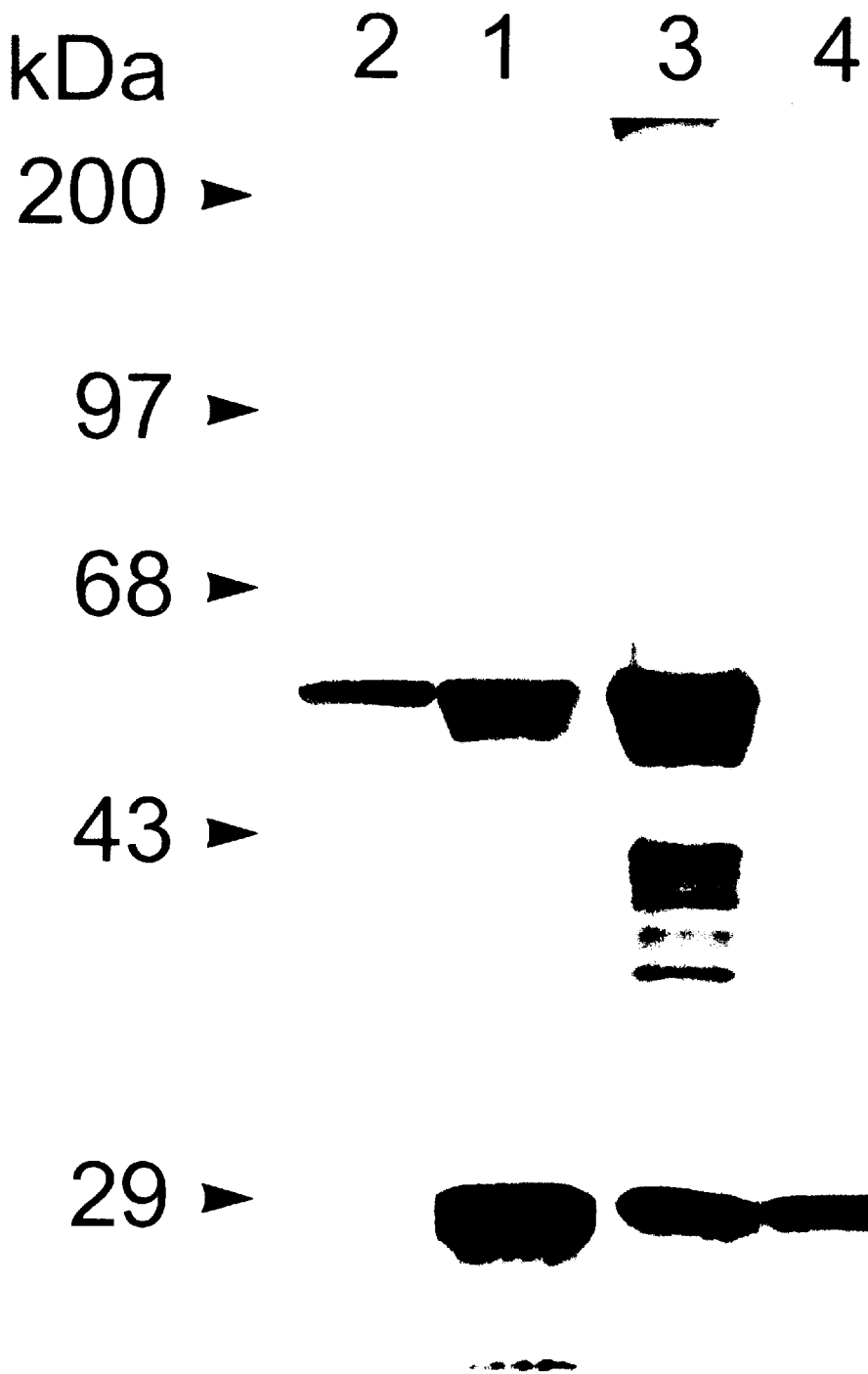
FIG. 5 shows expression of HPV11 L1 protein in yeast by Western analysis (immunoblot).

Samples containing 20 μg of total cellular protein were electrophoresed through 10% Tris-Glycine gels (Novex, Inc.) under denaturing conditions and electroblotted onto nitrocellulose filters. L1 protein was immunodetected using rabbit antiserum raised against a trpE-HPV11 L1 fusion protein as primary antibody (Brown, D. R. et al., 1994, *Virology* 201:46–54) and horseradish peroxidase (HRP)-linked donkey anti-rabbit IgG (Amersham, Inc.) as secondary antibody. The filters were processed using the chemiluminescent ECL™ Detection Kit (Amersham, Inc.). A 50–55 kDa L1 protein band was detected in all samples except the pGAL1-10 negative control (lane 4) (FIG. 5). Furthermore, the amount of HPV11 L1 protein expressed by the HPV6/11 hybrid gene (lane 3) appears to be ~10-fold greater than the amount of L1 protein expressed by either the wt-HPV11 gene (lane 2) or the HPV6 L1 gene (lane 1).

EXAMPLE 9
ELISA of Yeast Expressed HPV11 L1 VLPs

An ELISA was used to determine relative amounts of VLPs produced from yeast clones expressing either wt-HPV11 or the HPV6/11 hybrid. The ELISA was also used to demonstrate that a conformational epitope giving rise to strongly neutralizing antibody responses was retained on the VLPs derived from the HPV6/11 hybrid DNA. This conformational epitope has been defined by monoclonal antibody H11.B2 (Christensen et al 1990, *J. Virol.* 64, 5678–5681) which is available from Chemicon International (Temecula, Calif.) as Chemicon Mab8740. Briefly, wells of ELISA plates (Maxisorb, Nunc Inc., Naperville, Ill.) were coated with decreasing amounts of total yeast protein containing the HPV6/11 (hybrid) or wt-HPV11 VLPs in 100 μL PBS. CsCl-purified wt-HPV11 virions (a generous gift of Dr. D. Brown) and control yeast protein were used as controls. The plates were incubated overnight at 4° C. before aspirating and blocking the plates with 250 mcl 10% dried milk (Carnation) in TTBS (50 mM Tris, pH 7.6, 150 mM NaCl, 0.1% Tween20) for 2 hrs at room termperature. The plates were washed once with PBS/0.1% Tween 20 before incubating the wells with 100 mcl of a 1:1000 dilution of the anti-HPV11 virion monoclonal antibody Chemicon MAB 8740 in 1% dried milk in TTBS for 1 hr at room temperature. Plates were washed 3 times with PBS/Tween 20 and then incubated with 100 mcl of anti-mouse IgG coupled to alkaline phosphatase (Kierkegard & Perry, Gaithersburg, Md.) at a dilution of 1:1000 in 1% milk+TTBS for 1 hr at room temperature. Plates were again washed 3 times with PBS/Tween 20 before adding 100 mcl of phosphatase substrate (p-nitrophenyl phosphate in diethanolamine buffer). Plates were incubated 30 min at room temperature. The reaction was stopped by addition of 50 mcl of 3N NaOH. Plates were read at 405 nm in an ELISA plate reader.

Figure 6:
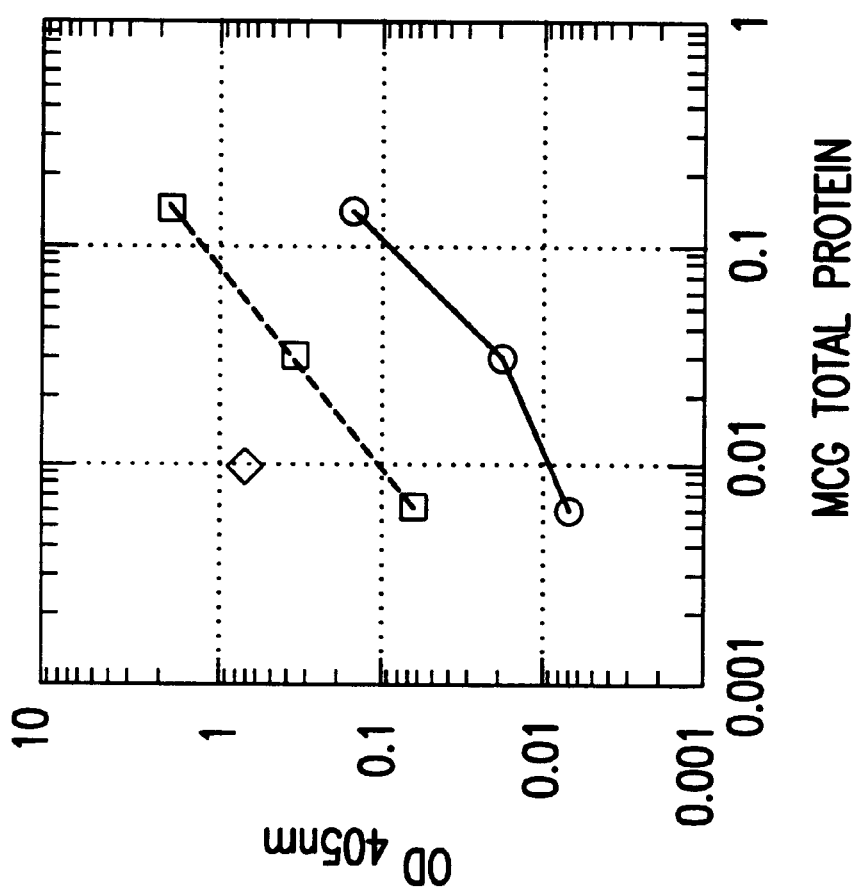
FIG. 6 shows ELISA reactivities of HPV11 L1 VLPs expressed from wild-type (wt) HPV11 compared to HPV6/11 hybrid DNA.

The average $OD_{405\ nm}$ readings of 2 wells corrected against the background readings obtained from control yeast proteins were plotted against the total yeast protein in the wells and are shown in FIG. 6. The HPV6/11 hybrid yeast clone produced more than 10 times the amount of native VLPs compared to the wt clone. In addition, the strongly neutralizing epitope recognized by Chemicon Mab 8740 is displayed on these VLPs.

EXAMPLE 10
Electron Microscopic Studies

Figure 7:
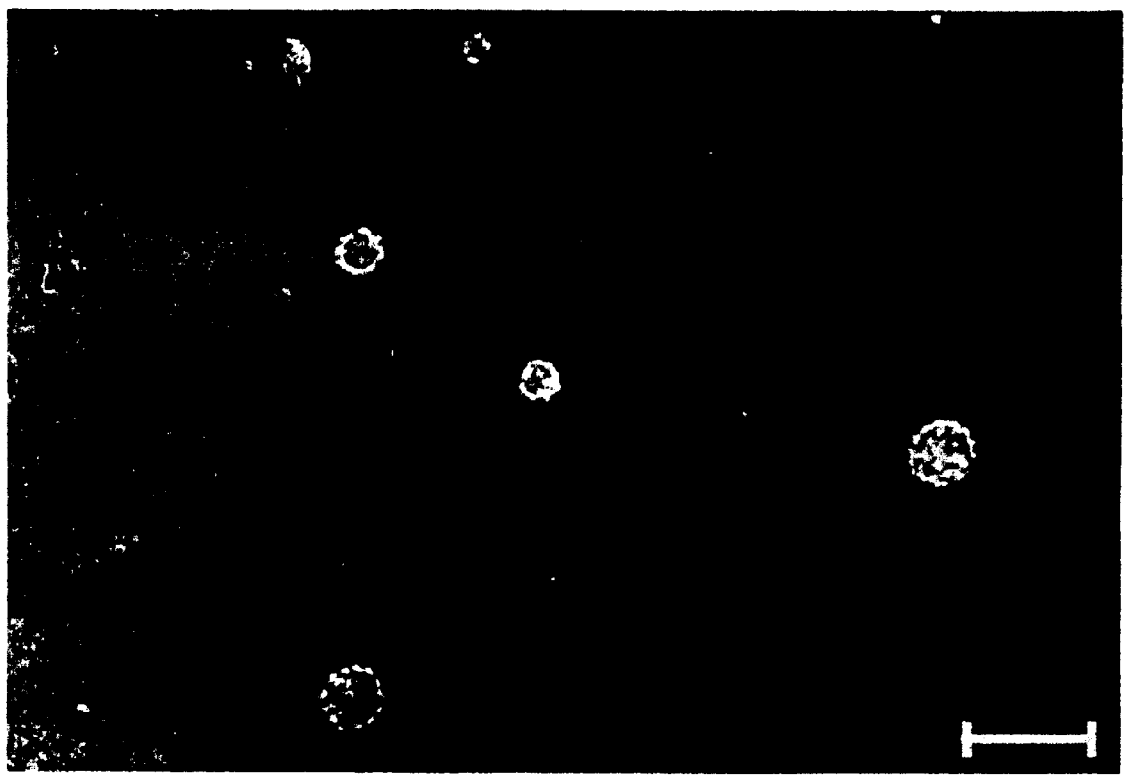
FIG. 7 is an electron micrograph of HPV11 L1 VLPs expressed in yeast.

For EM analysis (Structure Probe, West Chester, Pa.), an aliquot of each sample (crude clarified lysate or purified VLPs) was placed on 200-mesh carbon-coated copper grids. A drop of 2% phosphotungstic acid (PTA), pH 7.0 was placed on the grid for 20seconds. The grids were allowed to air dry prior to transmission EM examination. All microscopy was done using a JEOL 100CX transmission electron microscope (JEOL USA, Inc.) at an accelerating voltage of 100 kV. The micrographs generated have a final magnification of 100,000×. As shown in FIG. 7, VLPs were observed in the 45–55 nm diameter size range in all HPV11 samples but not in yeast control samples.

EXAMPLE 11
Fermentation of HPV6/11 L1 (Strain #1782)

Surface growth of a plate culture of strain 1782 was aseptically transferred to a leucine-free liquid medium containing (per L): 8.5 g Difco yeast nitrogen base without amino acids and ammonium sulfate; 0.2 g adenine; 0.2 g uracil; 10 g succinic acid; 5 g ammonium sulfate; and 0.25 g L tyrosine; this medium was adjusted to pH 5.0–5.3 with NaOH prior to sterilization. After growth for 25 hr at 28° C., 250 rpm on a rotary shaker, frozen culture vials were prepared by adding sterile glycerol to a final concentration of 17% (w/v) prior to storage at −70° C. (1 mL per cryovial). Inoculum for fermentation of strain 1782 was developed in the same medium (750 mL per 2-L flask) and was started by transferring the thawed contents of two frozen culture vials to the 2-L flasks and incubating at 28° C., 250 rpm on a rotary shaker for 25 hr. Fermentation of strain 1782 used a Chemap 23 L fermenter with a working volume of 18 L after inoculation. The production medium used contained (per L): 20 g Difco yeast extract; 10 g Sheffield HySoy peptone; 20 g glucose; 20 g galactose; the medium was adjusted to pH 5.3 prior to sterilization. The entire contents (500 mL) of the 2-L inoculum flask was transferred to the fermenter which was incubated at 28° C., 9 L air per min, 500 rpm, 3.5 psi pressure. Agitation was increased as needed to maintain dissolved oxygen levels of greater than 40% of saturation. Progress of the fermentation was monitored by off line glucose measurements (Beckman Glucose 2 Analyzer) and online mass spectrometry (Perkin-Elmer 1200). After 66 hr incubation, a cell density of 9.32 g dry cell weight per L was reached. The contents of two such fermentations (total 17.5 L broth) were pooled before cell recovery. The culture was concentrated by hollow fiber filtration (Amicon H5MP01-43 cartridge in an Amicon DC-10 filtration system) to ca. 2 L, diafiltered with 2 L phosphate-buffered saline, and concentrated further (to ca. 1 L) before dispensing into 500 mL centrifuge bottles. Cell pellets were collected by centrifugation at 8,000 rpm (Sorval GS3 rotor) for 20 min at 4° C. After decanting the supernatant, the pellets (total 358 g wet cells) were stored at −70° C. until use.

EXAMPLE 12
Purification of Recombinant HPV Type 11 L1 Capsid Proteins

All steps were performed at 4° C. unless noted.

Cells were stored frozen at −70° C. Frozen cells (wet weight=180 g) were thawed at 20–23° C. and resuspended in 900 mL "Breaking Buffer" (50 mM MOPS, pH 7.2, 500 mM NaCl, 1 mM $CaCl_2$). The protease inhibitors AEBSF and pepstafin A were added to final concentrations of 1 mM and 1.7 μM, respectively. The cell slurry was broken at a pressure of approximately 16,000 psi by 4 passes in a M110-Y Microfluidizer (Microfluidics Corp., Newton, Mass.). A sufficient volume of 10% Triton X100® detergent (Pierce, Rockford, Ill.) was added to the broken cell slurry to bring the concentration of TX100 to 0.5%. The slurry was stirred for 20 hours. The Triton X100-treated lysate was centrifuged at 12,000×g for 40 min to remove cellular debris. The supernatant liquid containing L1 protein was recovered.

The supernatant liquid was diafiltered against five volumes of 20 mM sodium phosphate, pH 7.2, 0.5M NaCl using a 300K tangential flow membrane cassette (Filtron, Northborough, Mass.). The material retained by the membrane was shown by radioimmunoassay and western blotting to contain the L1 protein.

The retentate was applied to a high resolution affinity column (11.0 cm ID×5.3 cm) of SP Spherodex (M)® resin (IBF, Villeneuve-la-Garenne, France) equilibrated in 20 mM sodium phosphate, pH 7.2, 0.5M NaCl. Following a wash with equilibration buffer and a step wash with 20 mM sodium phosphate, pH 7.2, 1.0M NaCl, the L1 protein was eluted with a step wash of 20 mM sodium phosphate, pH 7.2, 2.5M NaCl. Fractions were collected during the washes and elution. Column fractions were assayed for total protein by the Bradford method. Fractions were then analyzed by western blotting and SDS-PAGE with colloidal Coomassie detection. Fractions were also analyzed by radioinunnoassay.

SP Spherodex fractions showing comparable purity and enrichment of L1 protein were pooled.

Final product was analyzed by western blotting and SDS-PAGE with colloidal Coomassie detection. The L1 protein was estimated to be >90% homogeneous. The identity of L1 protein was confirmed by western blotting. The final product was filtered aseptically through a 0.22 μm membrane and stored at 4° C. This process resulted in a total of 100 mg protein.

Electron microscopy analysis is performed by Structure Probe (West Chester, Pa.). An aliquot of sample is placed on a 200 mesh carbon-coated copper grid. A drop of 2% phosphotungstic acid, pH 7.0 is placed on the grid for 20 seconds. The grid is allowed to air dry prior to TEM examination. All microscopy is performed using a JEOL 100 CX transmission electron microscope (JEOL USA, Inc.) at an accelerating voltage of 100 kV. The micrographs generated have a final magnification of 100,000×.

Bradford Assay for Total Protein

Total protein was assayed using a commercially available Coomassie Plus® kit (Pierce, Rockford, Ill.). Samples were diluted to appropriate levels in Milli-Q-$H_2O$. Volumes required were 0.1 mL and 1.0 mL for the standard and microassay protocols, respectively. For both protocols, BSA (Pierce, Rockford, Ill.) was used to generate the standard curve. Assay was performed according to manufacturer's recommendations. Standard curves were plotted using CricketGraph® software on a Macintosh IIci computer.

SDS-PAGE and Western Blot Assays

All gels, buffers, and electrophoretic apparatus were obtained from Novex (San Diego, Calif.) and were run according to manufacturer's recommendations. Briefly, samples were diluted to equal protein concentrations in Milli-Q-$H_2O$ and mixed 1:1 with sample incubation buffer containing 200 mM DTT. Samples were incubated 15 min at 100° C. and loaded onto pre-cast 12% Tris-glycine gels. The samples were electrophoresed at 125 V for 1 hr 45 min. Gels were developed by colloidal Coomassie staining using a commercially obtained kit (Integrated Separation Systems, Natick, Mass.).

For western blots, proteins were transferred to PVDF membranes at 25 V for 40 min. Membranes were washed with Milli-Q-H2O and air-dried. Primary antibody was polyclonal rabbit antiserum raised against a TrpE-HPV11 L1 fusion protein (gift of Dr. D. Brown). The antibody solution was prepared by dilution of antiserum in blotting buffer (5% non-fat milk in 6.25 mM Na phosphate, pH 7.2, 150 mM NaCl, 0.02% $NaN_3$). Incubation was for at least 1 hour at 20–23° C. The blot was washed for 1 min each in three changes of PBS (6.25 mM Na phosphate, pH 7.2, 150 mM NaCl). Secondary antibody solution was prepared by diluting goat anti-rabbit IgG alkaline phosphatase-linked conjugate antiserum (Pierce, Rockford, Ill.) in blotting buffer. Incubation proceeded under the same conditions for at least 1 hour. Blots were washed as before and detected using a 1 step NBT/BCIP substrate (Pierce, Rockford, Ill.).

EXAMPLE 13
Preparation of Immunogenic Compositions

Purified VLP's are formulated according to known methods, such as by the admixture of pharmaceutically acceptable carriers, stabilizers, or a vaccine adjuvant. The immunogenic VLP's of the present invention may be prepared for vaccine use by combining with a physiologically acceptable composition such as, e.g. PBS, saline or distilled water. The immunogenic VLP's are administered in a dosage range of about 0.1 to 100 mcg, preferably about 1 to about 20 mcg, in order to obtain the desired immunogenic effect. The amount of VLP per formulation may vary according to a variety of factors, including but not limited to the individual's condition, weight, age and sex. Administration of the VLP formulation may be by a variety of routes, including but not limited to oral, subcutaneous, topical, mucosal and intramuscular. Such VLP formulations may be comprised of a single type of VLP (i.e., VLP from HPV11) or a mixture of VLP's (i.e, VLP's from HPV6, HPV11, HPV16 and HPV18).

An antimicrobial preservative, e.g. thimerosal, optionally may be present. The immunogenic antigens of the present invention may be employed, if desired, in combination with vaccine stabilizers and vaccine adjuvants. Typical stabilizers are specific compounds, e.g. polyanions such as heparin, inositol hexasulfate, sulfated beta-cyclodextrin, less specific excipients, e.g. amino acids, sorbitol, mannitol, xylitol, glycerol, sucrose, dextrose, trehalose, and variations in solution conditions, e.g. neutral pH, high ionic strength (ca. 0.5–2.0M salts), divalent cations ($Ca^{2+}$, $Mg^{2+}$). Examples of adjuvants are $Al(OH)_3$ and $Al(PO_4)$. The vaccine of the present invention may be stored under refrigeration or in lyophilized form.

EXAMPLE 14
Preparation of Antibodies to VLP

Purified VLP are used to generate antibodies. The term "antibody" as used herein includes both polyclonal and monoclonal antibodies as well as fragments thereof, such as Fv, Fab and F(ab)2 fragments that are capable of binding antigen or hapten. The antibodies are used in a variety of ways, including but not limited to the purification of recombinant VLP, the purification of native L1 or L2 proteins, and kits. Kits would comprise a compartmentalized carrier suitable to hold in close confinement at least one container. The carrier would further comprise reagents such as the anti-VLP antibody or the VLP suitable for detecting HPV or fragments of HPV or antibodies to HPV. The carrier may also contain means for detection such as labeled antigen or enzyme substrates or the like. The antibodies or VLP or kits are useful for a variety of purposes, including but not limited to forensic analyses and epidemiological studies.

What is claimed is:

1. An isolated and purified DNA molecule encoding human papillomavirus type 11 L1 protein, the DNA molecule being free of internal transcription termination signals which are recognized by yeast.

2. The DNA molecule of claim 1 having the sequence shown in FIG. 8 SEQ. ID. NO.38.

3. An expression vector comprising the DNA molecule of claim 1.

4. A composition comprising the DNA molecule of claim 1, or RNA complementary to the DNA molecule of claim 1.

5. An expression vector comprising the DNA molecule of claim 2.

6. The expression vector of claim 5 which is D362-1.

7. A nucleic acid encoding human papillomavirus type 11 L1 protein, the nucleic acid molecule being free from internal transcription termination signals which are recognized by yeast.

* * * * *